United States Patent
Moskowitz et al.

(10) Patent No.: US 8,895,940 B2
(45) Date of Patent: Nov. 25, 2014

(54) SWITCH SANITIZING DEVICE

(71) Applicants: Jay Moskowitz, Mechanicsburg, PA (US); Michael Randall, Simpsonville, SC (US)

(72) Inventors: Jay Moskowitz, Mechanicsburg, PA (US); Michael Randall, Simpsonville, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/195,357

(22) Filed: Mar. 3, 2014

(65) Prior Publication Data

US 2014/0252247 A1   Sep. 11, 2014

Related U.S. Application Data

(60) Provisional application No. 61/851,281, filed on Mar. 5, 2013.

(51) Int. Cl.
*A61L 2/10* (2006.01)

(52) U.S. Cl.
CPC ..................................... *A61L 2/10* (2013.01)
USPC .................................. 250/455.11; 422/186.3

(58) Field of Classification Search
USPC .......... 250/455.11, 454.11; 422/22, 24, 186.3
See application file for complete search history.

(56) References Cited

U.S. PATENT DOCUMENTS

| | | | |
|---|---|---|---|
| 2,756,470 A | 3/1953 | Sawchuk | |
| 3,314,746 A | 4/1967 | Millar | |
| 6,605,260 B1 | 8/2003 | Busted | |
| 6,923,367 B1 | 8/2005 | Grossman et al. | |
| 7,692,172 B2 | 4/2010 | Leben | |
| 7,834,335 B2 | 11/2010 | Harmon et al. | |
| 7,888,657 B1 * | 2/2011 | Zadro | 250/455.11 |
| 7,989,779 B1 | 8/2011 | Ray et al. | |
| 8,087,737 B2 | 1/2012 | Shoenfeld | |
| 8,097,861 B2 | 1/2012 | Leben | |
| 8,143,596 B2 | 3/2012 | Yerby | |
| 8,598,539 B2 | 12/2013 | Chuang | |
| 2006/0120915 A1 | 6/2006 | Lewandowski | |
| 2007/0258852 A1 | 11/2007 | Hootsmans et al. | |
| 2008/0197226 A1 | 8/2008 | Cooper et al. | |
| 2008/0213128 A1 | 9/2008 | Rudy et al. | |
| 2010/0102252 A1 | 4/2010 | Harmon et al. | |
| 2011/0158862 A1 | 6/2011 | Kim et al. | |
| 2011/0256019 A1 | 10/2011 | Gruen et al. | |
| 2011/0291995 A1 | 12/2011 | Shr et al. | |
| 2012/0181447 A1 | 7/2012 | Yerby | |

(Continued)

FOREIGN PATENT DOCUMENTS

| | | |
|---|---|---|
| KR | 1020070098525 | 10/2007 |
| KR | 100996465 | 11/2010 |
| WO | WO 00/41734 | 7/2000 |

*Primary Examiner* — Kiet T Nguyen

(74) *Attorney, Agent, or Firm* — Dority & Manning, P.A.

(57) ABSTRACT

The invention relates to a family of devices to be used for sanitizing switches. The device is placed around the periphery of the switch and contains a means for exposing the switch touch surfaces to UV light source local to the switch in order to maximize the exposure of the switch to the UV light source. Because the light is localized and directed toward the switch contact surfaces, the device may be used continuously while humans or animals are present without detrimental exposure to the UV light, ensuring a sanitary switch contact surface so as to reduce or prevent infection or disease resulting from transference of contamination from one person to another via contact transference with said switch surface.

20 Claims, 13 Drawing Sheets

(56) References Cited

U.S. PATENT DOCUMENTS

2012/0217415 A1    8/2012    Wormely
2012/0240968 A1    9/2012    Schumacher
2012/0241284 A1    9/2012    Kobayashi et al.

\* cited by examiner

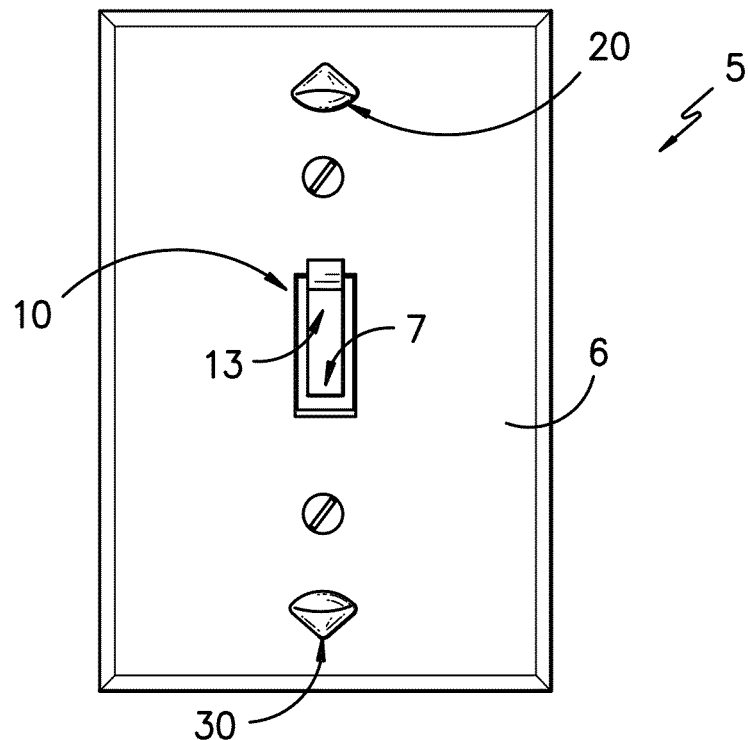
FIG. -11-
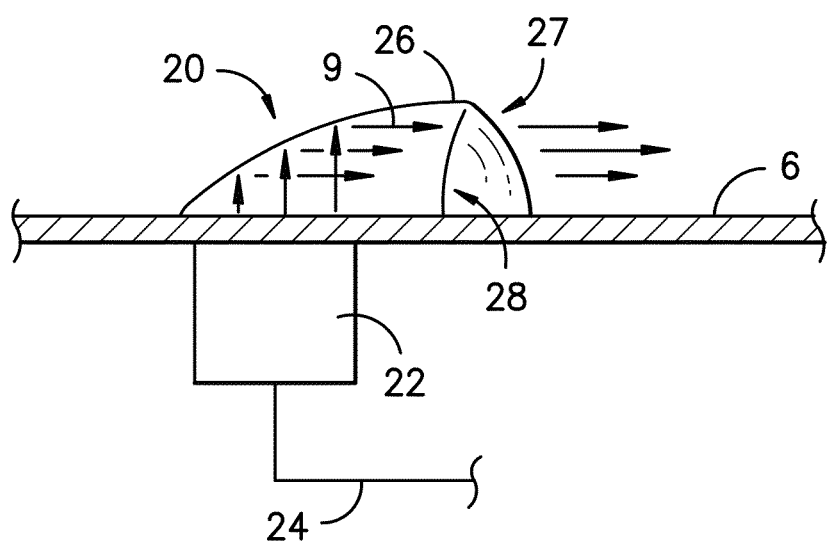
FIG. -12-

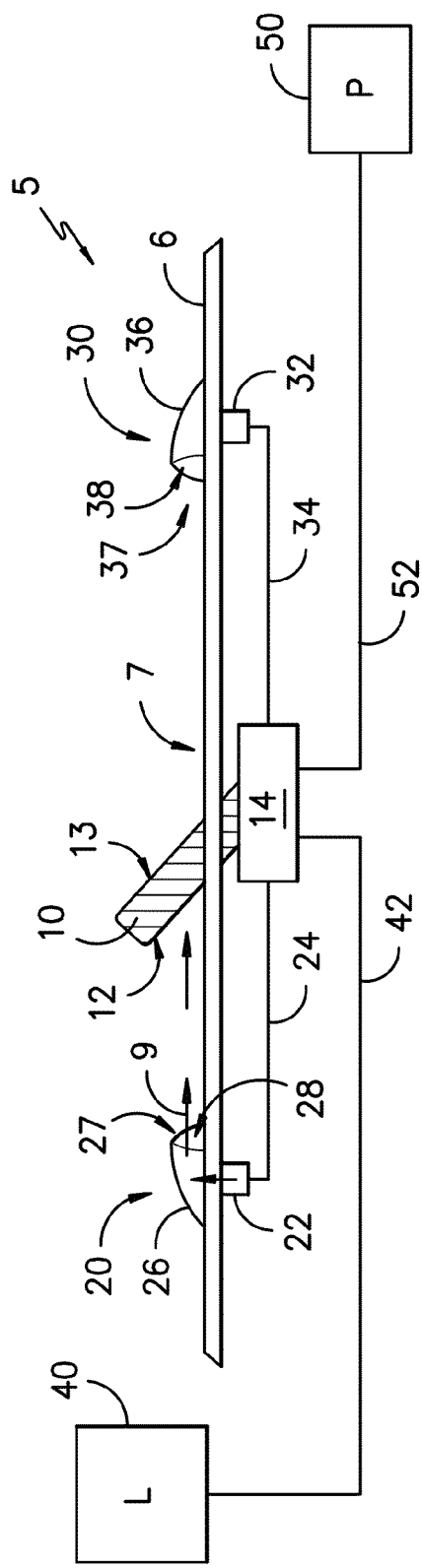
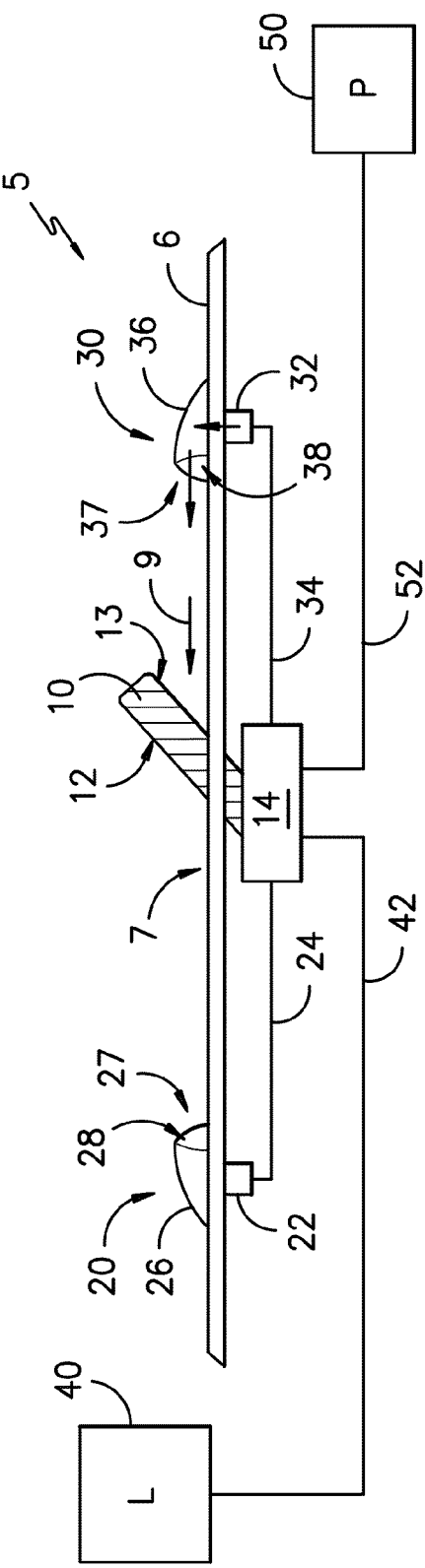
FIG. -13A-
FIG. -13B-

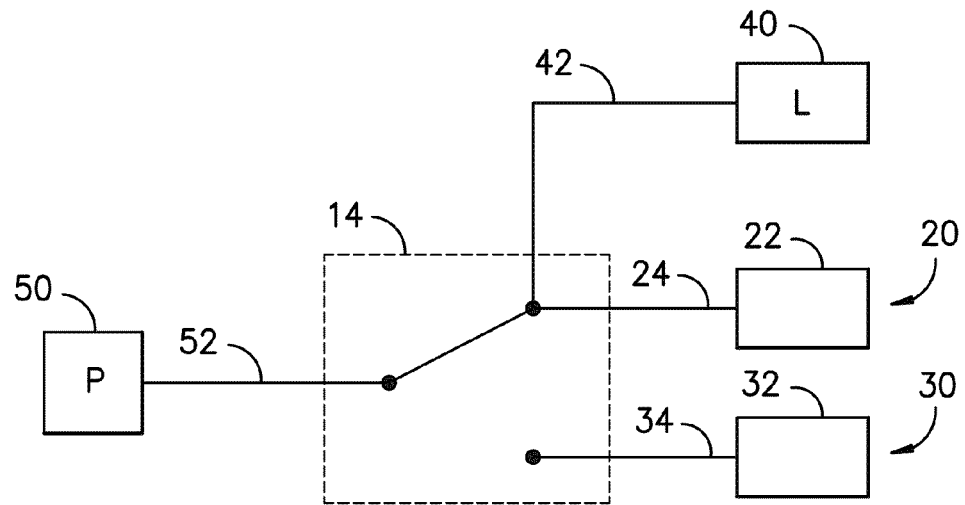
FIG. -14A-
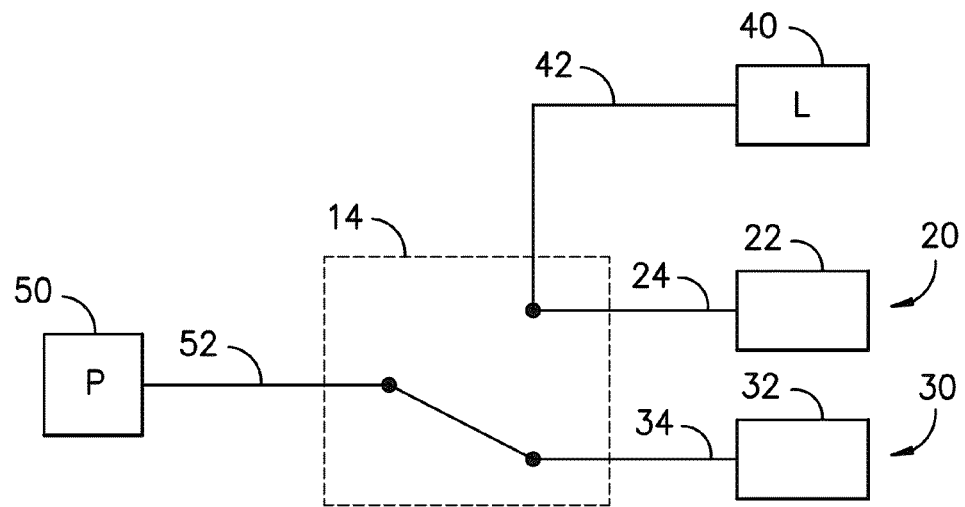
FIG. -14B-

SWITCH SANITIZING DEVICE

PRIORITY INFORMATION

The present application claims priority to U.S. Provisional Patent Application Ser. No. 61/851,281 titled "Switch Sanitizing Device" of Moskowitz, et al. filed on Mar. 5, 2013, the disclosure of which is incorporated by reference herein.

FIELD OF THE INVENTION

The present invention relates to UV light sources that are designed to bathe or expose switch contact surfaces in UV light. The invention combines the germicidal or sanitizing effectiveness of UV electromagnetic radiation, with novel routing and shield of said radiation in a region local to the switch contact surface so as to sanitize the contact surface of the switch or switches of interest without harmful or significant exposure of humans or animals to the UV radiation.

BACKGROUND OF THE INVENTION

Infectious disease (ID) transmission by way of contact transmission is a significant problem. The most important and frequent mode of transmission of nosocomial infections is by direct contact. Contact transmission may occur either through direct contact with an infected person (direct contact transmission) or may occur by way indirect contact transmission which involves contact of a susceptible host with a contaminated intermediate object that is typically in a public or common area of usage. These contact surfaces are often easily contaminated and may represent vectors for contamination that can lead to the spread of disease through contact transference of contamination.

Light switches, elevator call buttons, elevator panel buttons, security key pads, toilet flush switch buttons are a few examples of contact surfaces that are typical vectors for indirect contact transmission of infectious disease. For example, influenza viruses may be transferred via indirect contact transmission. It is estimated by the US Center for Disease Control (CDC) that influenza viruses affect 5% to 20% of the U.S. population each year. The CDC also estimates that more than 200,000 people a year are hospitalized due to flu complications, and approximately 36,000 die from influenza related infection.

Contamination, such as an influenza virus, transfers indirectly from an infected person or object to another person by way of a contaminated touch surface. Said contamination can enter one's body when hands that have previously touched an infected touch surface also touch the mouth, nose or other area of entry for the contaminant to enter one's body. Other contaminants, that are easily transferred via indirect contact transference include, but are not limited to bacteria such as Methicillin-Resistant *Staphylococcus Aureus* (MRSA), or *Clostridium Difficile* (C. dif. or CDF), or the like.

Contact transference of contamination can be especially problematic in hospitals and other care facilities as well as in heavily trafficked public areas such as subway stations or the like. These communal facilities are characterized by numerous contamination vectors, many of which involve indirect contamination transference from one person to another via touch surfaces.

As an example, according to the CDC, approximately 1 out of every 20 hospital patients will experience a hospital acquired infection (HAI) and cost U.S. hospitals as much as $45 B per annually. In 2002 the estimated number of HAIs in U.S. hospitals was estimated to be 1.7 M with nearly 100,000 of these HAIs resulting in death with the average cost per HAI on the order of $25,000 (2002 basis). HAI has become such a significant expense that section 5001(c) of the Deficit Reduction Act states that hospitals will no longer receive reimbursement from CMS for selected conditions related to HAI, adding significant economic burden to numerous U.S. hospitals.

Unfortunately, many of the potential contamination transference vectors characteristic of healthcare facilities and public or common areas are not adequately addressed. It is an object of the present invention to enable the reduction or elimination of transference related contamination from select touch points, including but not limited to electrical switches, and push button switches, such as common light switches, elevator call buttons, elevator panel buttons, toilet flush switches or buttons and the like, in a manner that is efficient, effective and economical.

Electrical or electronic switches (such as light switches, elevator switches, and the like), in common areas such as hotels, typically are contaminated. Said contamination may be transferred from one user of the switch to another at the contact surface of the switch when it is used. This contamination transference vector is thought to contribute to the transfer of myriad communicable diseases. Thus, an effective means of keeping the contact surfaces of switches disinfected is needed.

Manual cleaning of switches is the current state of the art for disinfecting switch contact surfaces. This method requires diligence in order to insure that the entire contact surface of each switch is disinfected. This method is labor intensive, and is therefore costly. It also is typically not consistent and validation tools, such as testing the contact surface after cleaning for microbial substances, are typically not used to verify that cleaning was effective. Additionally, since cleaning is not typically performed after each contact, there is no way to ensure that the surface is disinfected with each contact.

Other methods include use of antiseptic sprays or chemical foggers (e.g., peroxide "bombs" and the like). These methods typically are used to disinfect an entire enclosure and thus, are expensive and must be applied frequently. Additionally, since these disinfection methods are not typically performed after each contact, there is no way to ensure that the surface is disinfected prior to each contact.

Use of UV light has been shown to be effective at killing or passivation of most microbial substances that are known to cause infection or disease. Ultraviolet or UV light is typically divided into three subcategories depending upon the wavelength of the light or electromagnetic radiation comprising the spectrum of said light. These categories are typically known as UV A, UV B or UV C. UV A is generally comprised of wavelengths of electromagnetic radiation mainly in the range of 315 nm to 400 nm, while UV B is generally comprised of wavelengths of electromagnetic radiation mainly in the range of 280 nm to 315 nm and UV C is generally comprised of wavelengths of electromagnetic radiation (EM) mainly in the range of 100 nm or 200 nm to 280 nm. Of these three types of ultraviolet electromagnetic radiation, UV C is generally considered to have the greatest efficacy in killing or in passivating germs that are responsible for disease or infection. For example, germicidal UV radiation of 254 nm wavelength is generally accepted to begin killing or passivating microbes with an exposure of about 2,000 $\mu W\text{-}s/cm^2$ with complete elimination or passivation occurring by exposures in the range of about 12,000 $\mu W\text{-}s/cm^2$. Additionally, wavelengths of EM in the UV C range, especially near and below 100 nm to 200 nm can create ozone that is also an effective germicide. As a result, an effective means of disinfection has been termed UVGI or ultraviolet germicidal irradiation, which uses UV C to effectively kill or passivate surfaces from germs that cause disease or infection.

Unfortunately, UV C also has issues. It is attenuated at a relatively high rate in Earth's atmosphere. It is also harmful to the eyes and skin of humans and animals. Any ozone generated may also be destructive to the lungs of humans or animals. The availability of UV C light sources is also limited and UV C light sources tend to be expensive, relatively inefficient and low powered. Therefore it is important that the UV C source used to disinfect a surface be in close proximity to the surface and that the UV C irradiation be as direct as practicable, and of an appropriate intensity, duration and overall exposure in order to impart sufficient radiation to the surface so as to ensure sufficient sanitization of said surface. It is also important that the UV C radiation be contained enough such that the risk of deleterious exposure to humans or animals is kept to levels that are not significant enough to cause harm to humans or animals. Therefore, it is important to use UV C lights that are of relatively low intensity, that are in close proximity and with suitable angle of incidence to the surface of interest to be decontaminated. It is also important that the UV C source used to sanitize switch contact surfaces be designed to largely contain the UV C radiation so as to minimize UV C exposure of humans and animals to levels that are insignificant.

Several patents that are of interest to the present invention are discussed below. U.S. Pat. Nos. 7,692,172 and 8,097,861, by Leben, teach of a system used to sanitize an enclosed structure using a germicidal ultraviolet light source. The invention sanitizes the entire, human sized enclosure and utilizes at least two sensors, the first to detect the presence or absence of humans or animals within the enclosure and the second to detect the position of the door of the enclosure. The system taught in the patent would be unnecessarily expensive, requiring UV light sources of relatively high intensity, complex electronic logic systems and sensors and only works in the absence of humans or animals, thus not always ensuring a sanitized enclosure when used (e.g., if an elevator is continuously used, the sensors would constantly detect either the presence of humans or animals, or would detect that the door to the enclosure is open or both, and the sanitizing system would not be activated even though the enclosure may be contaminated and need to be sanitized. Additionally, this system is limited in the case of an elevator or the like as it would do nothing to sanitize anything outside the elevator enclosure (e.g., the elevator call buttons or the like).

U.S. Pat. No. 8,143,596 and Published US Patent Application US 2012/0181447, by Yerby, teach of a rigid opaque enclosure open at a door side thereof. An enclosure door is adapted to selectively close the door side of the enclosure. At least one UV bulb is fixed to at least one bulb fixture within the enclosure and extends at least partially into the open internal space of the enclosure. A cage is fixed around each sanitizer bulb. An article fastener is fixed with the cage and is adapted to be selectively fastened to the article for securing the article thereto. An electronic circuit is electrically connected to each sanitizer bulb and is adapted to power each bulb for a present period of time. A switch may be included proximate the door and adapted to electrically close when the door is closed to prevent bulb activation when the door is open. A wheeled support stand may be fixed with the enclosure. The device taught is useful for improving exposure of the article to be sanitized, and thus the sanitizing process especially in the regions of the article where sanitizing is most needed, since the UV light source is in a relatively close proximity to said article and said regions. However, the device described in the patent is rigid and opaque and cannot be used in a manner that allows human or animal access to a contact surface that is inside the volume exposed during the sanitizing process. Thus a switch or other object requiring manual human interaction could not be operated in a normal manner without opening or removing the rigid opaque enclosure from said object thus making it impractical to sanitize the contact surface of said object after each use.

U.S. Pat. No. 7,834,335, and published US Patent Application US 2010/0102252 by Harmon and Douglas teach a convenient mobile sterilization device that provides secure storage in a niche in a protective housing using a one-button action to automatically deploy and activate the sanitizing device for quick and powerful destruction of germs on a surface using one hand. Users can hold the UV-light device and move it across a target surface to sterilize or disinfect the surface. The device may be compact, easily deployed, provided with a durable cover for secure storage, and equipped with safety shut-off features to prevent unwanted uses. The invention taught is useful for sterilization of small objects and is small. However, the device described in the patent completely encloses the object to be sanitized and thus cannot be used in a manner that allows human or animal access to a contact surface that is inside the volume exposed during the sanitizing process. Thus a switch or other object requiring manual human interaction could not be operated in a normal manner without opening or removing the rigid enclosure from said object, thus making it impractical to sanitize the contact surface of said object after each use.

U.S. Pat. No. 6,923,367 by Grossman and Schumann, teaches of a safety mailbox system including a mailbox container integrated with at least one decontaminating mechanism. Contaminants may include chemical and biological agents. The invention taught is useful for sterilization of mail and likely could be modified to effectively disinfect myriad small objects. However, the device described in the patent completely encloses the object to be sanitized and thus cannot be used in a manner that allows human or animal access to a contact surface that is inside the volume exposed during the sanitizing process. Thus a switch or other object requiring manual human interaction could not be operated in a normal manner without opening or removing the rigid enclosure from said object, thus making it impractical to sanitize the contact surface of said object after each use.

U.S. Pat. No. 6,605,260 by Busted, teaches of an apparatus for sterilizing a member that includes a housing, with an enclosure defined therein, a source of ultraviolet light for illuminating the member, and an ozone source. A pump is connected to the ozone source to force the ozone to flow within the enclosure, and a heating device heats the ozone flow. The invention taught is useful for sterilization of myriad small devices. However, the device described in the patent completely encloses the object to be sanitized and thus cannot be used in a manner that allows human or animal access to a contact surface that is inside the volume exposed during the sanitizing process. Thus a switch or other object requiring manual human interaction could not be operated in a normal manner without opening or removing the rigid enclosure from said object, thus making it impractical to sanitize the contact surface of said object after each use.

Published US Patent Application 2011/0291995 by Shr, et al., teaches of a sterilizing device comprising a light guiding member and an ultraviolet (UV) light source. The light guiding member has a surface. The UV light source emits UV light rays such that the UV light rays are guided into the guiding member based on total internal reflection. When an object contacts or comes close to the surface, an evanescent wave from the UV light rays irradiates on the object. This device may be useful for sanitizing a contact surface, but the surface to be sanitized necessarily must be a light guide having total internal reflection. This is impractical in the case of the contact surface of a switch as it would be unnecessarily large and complex and would require replacement of the switch in the case of a retrofitting application. Specialized materials would be necessary as well and the efficacy of this device for sanitizing is unproven. Additionally, the danger of UV exposure to humans or animals by this device is questionable.

Published US Patent Application 2011/0158862, by Kim, et al., teaches of an escalator handrail sterilizer which is installed close to an inlet or outlet of an escalator handrail, and cleans and sterilizes the handrail moving in or out. The sterilizer comprises a case which is prepared for surrounding the escalator handrail, a chemical spray unit which is prepared in one end inside the case to spray chemicals on the handrail moving in, an ultraviolet ray irradiation unit which is prepared in the other end inside the case to project ultraviolet rays on the chemical-sprayed handrail, a drying unit which dries the chemicals sprayed on the handrail, a control unit which controls the chemical spray unit, the UV irradiation unit and the drying unit, and a cover which is prepared in both ends of the case in order to prevent foreign materials from flowing into the case. This device, while highly valuable for sanitizing a moving handrail as used on an escalator, would not be suitable for sanitizing a switch contact surface as it requires that the surface to be sanitized move through the sanitizing unit and it would be impractical to move the switch or the sanitizing unit in this manner between each use of said switch.

Published US Patent Application 2007/0258852, by Hootsmans, et al., teaches of a passenger interface device that includes at least one input member having a contact surface that is adapted to be touched by an individual. A disinfectant is on the contact surface and the disinfectant comprises a radiation-activated material. A source of radiation irradiates the disinfectant to disinfect the contact surface of the passenger interface device. In one example, titanium dioxide is used as a photo-catalyst that disinfects the contact surface responsive to ultraviolet light radiation. This device requires that a permanent disinfectant coating on the contact surface of the switch and that it be irradiated with a light source. One embodiment irradiates the contact surface from behind, requiring the light of suitable intensity to activate the disinfectant. This would necessitate that the light illuminate directly outward from the contact surface which could provide hazardous exposure to humans or animals. Additionally, the disinfectant coating may be impractical to use, requiring switch replacement or difficult and expensive application of the coating that may result in non-satisfactory appearance or functionality. Furthermore, proper use of high energy radiation (UV C or the like) does not require a photo-catalyst or other disinfectant coating in order to sanitize a surface.

Published US Patent Application 2012/0241284, by Kobayashi, et al., teaches of a sterilization and cleaning device of an escalator including a hand rail; a plasma source for irradiating the hand rail with ions or radicals or UV light; and enclosure for housing plasma; a fan for generating relatively negative pressure in the enclosure; filter units for removing removed bacteria, viruses and organic matter such as hand marks; and filter plates located backward and forward of a moving direction of the hand rail in the enclosure along the hand rail. This device is for sanitizing a moving handrail as used on an escalator. As such, it would not be suitable for sanitizing a switch contact surface as it requires that the surface to be sanitized move through the sanitizing unit and it would be impractical to move the switch or the sanitizing unit in this manner between each use of said switch.

Published US Patent Application 2012/0217415, by Wormely, teaches of a device named the "Clean as a Whistle Cleaning System", which is claimed to be a product that will sanitize and deodorize whistles with the use of a liquid. Accordingly the product accomplishes this goal by the use of unique ultraviolet bulb. The bulb is powered by AA batteries which work in conjunction with the circuit board. The compact and very portable units are equipped with a power button that starts the cleaning process and automatically shuts off the units after the cleaning process has been completed. The process is claimed to take no longer than 15 minutes to complete. In addition, it is claimed that the units are also designed to so additional sanitized whistles. The invention taught is useful for sterilization of whistles and could likely be applied to clean the contact surfaces of myriad small objects. However, the device described in the patent completely encloses the object to be sanitized and thus cannot be used in a manner that allows human or animal access to a contact surface that is inside the volume exposed during the sanitizing process. Thus a switch or other object requiring manual human interaction could not be operated in a normal manner without opening or removing the rigid enclosure from said object, thus making it impractical to sanitize the contact surface of said object after each use.

Published US Patent Application US 2008/0197226, by Cooper and Chen, teaches of a cord reel sanitizer that includes a spool for windingly receiving a cord within a spool housing interior and a sanitizer for sanitizing the spool housing interior. According to one embodiment, the sanitizer includes an ultraviolet lamp generating ultraviolet radiation, most preferably having a wavelength between approximately 250 and 260 nanometers, and a reflector redirecting ultraviolet radiation toward the spool housing interior. A control system for activating the sanitizer may include a manual actuation switch or, alternatively, may sense when a cord is unwound from the spool to activate the sanitizer. The control system may be adapted to activate the sanitizer during a predetermined activation time period. The control system may include a light indicator for visually signaling during activation of the sanitizer. The spool housing may define first and second cord openings for respective passage of first and second ends of a cord to an exterior of the spool housing. The device described in the patent completely encloses the object to be sanitized and thus cannot be used in a manner that allows human or animal access to a contact surface that is inside the volume exposed during the sanitizing process. Thus a switch or other object requiring manual human interaction could not be operated in a normal manner without opening or removing the rigid enclosure from said object, thus making it impractical to sanitize the contact surface of said object after each use. This device would not be suitable for sanitizing a switch contact surface as it requires that the surface to be sanitized move into and out of the sanitizing unit in order to be used and it would be impractical to move the switch or the sanitizing unit in this manner between each use of said switch.

U.S. Pat. No. 8,598,539, by Chuang, teaches of a germicidal device for elevator buttons includes a casing and a lamp tube installed inside the casing and capable of emitting germicidal light. The casing can be fixedly mounted on an elevator control panel for the germicidal light emitted from the lamp tube to project onto all elevator buttons on the elevator control panel, so as to continuously kill any germs on the elevator buttons. The casing is provided on a bottom with an elongated slot, via which the germicidal light emitted from the lamp tube is outward projected onto all the elevator buttons. The lamp tube can be a UV germicidal lamp tube for emitting UV germicidal light. The device taught in the patent has several major drawbacks. The UV light source illuminates from one direction only such that elevator buttons nearest said source receive a much greater level of germicidal UV radiation than the button further from said source. Additionally, the angle of incidence of said UV radiation is extremely low, if not completely horizontal. Thus, the intensity of the light source used would have to be extremely, if not infinitely large. Additionally, this approach will not work if the elevator buttons are flush mounted or recess mounted or the like as the UV radiation will be shielded by the panel. Additionally, anyone using any of the elevator buttons would be exposed to a potentially prohibitive dose of UV radiation as the UV light source would have to be extremely, if not infinitely intense in order to have any germicidal effect upon the elevator buttons at all.

As such, a need exists for an improved sanitizing device for use with a switch or other contact surfaces.

SUMMARY OF THE INVENTION

Objects and advantages of the invention will be set forth in part in the following description, or may be obvious from the description, or may be learned through practice of the invention.

In one aspect, the present subject matter is directed to a switch sanitizing device. The device may generally include a plate defining a switch aperture and a switch extending through the switch aperture. The switch may be moveable between an off-position and an on-position. In addition, the switch may include a first sanitizing source positioned on the device such that UV electromagnetic radiation from the first sanitizing source is directed to a first contact surface area on the switch and a second sanitizing source positioned on the device such that UV electromagnetic radiation from the second sanitizing source is directed to a second contact surface area on the switch.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 3 is a perspective view of a third illustrative example of the invented switch sanitizer, in accordance with the present invention, designed for use with a push button type switch such as an elevator call button or the like.

FIG. 4 is a front view of a fourth illustrative example of the invented switch sanitizer, in accordance with the present invention, designed for use with one or more push button type switch(es) such as an elevator panel or similar switch array or the like.

FIG. 5 is a front view of a fifth and a sixth illustrative example of the invented switch sanitizer, in accordance with the present invention, designed for use with one or more push button type switch(es) such as an elevator panel or similar switch array or the like.

FIG. 11 shows another exemplary switch sanitizer device having a pair of sanitizing lights positioned opposite a light switch.

FIG. 12 shows a cross-sectional view of an exemplary sanitizing light for use in the embodiment shown in FIG. 11.

FIG. 13A shows a cross-sectional view of the exemplary switch sanitizer device of FIG. 11 in an on-position.

FIG. 13B shows a cross-sectional view of the exemplary switch sanitizer device of FIG. 11 in an off-position.

FIG. 14A shows an electrical diagram of the exemplary switch sanitizer device of FIG. 11 in the on-position.

FIG. 14B shows an electrical diagram of the exemplary switch sanitizer device of FIG. 11 in the off-position.

Figure 1:
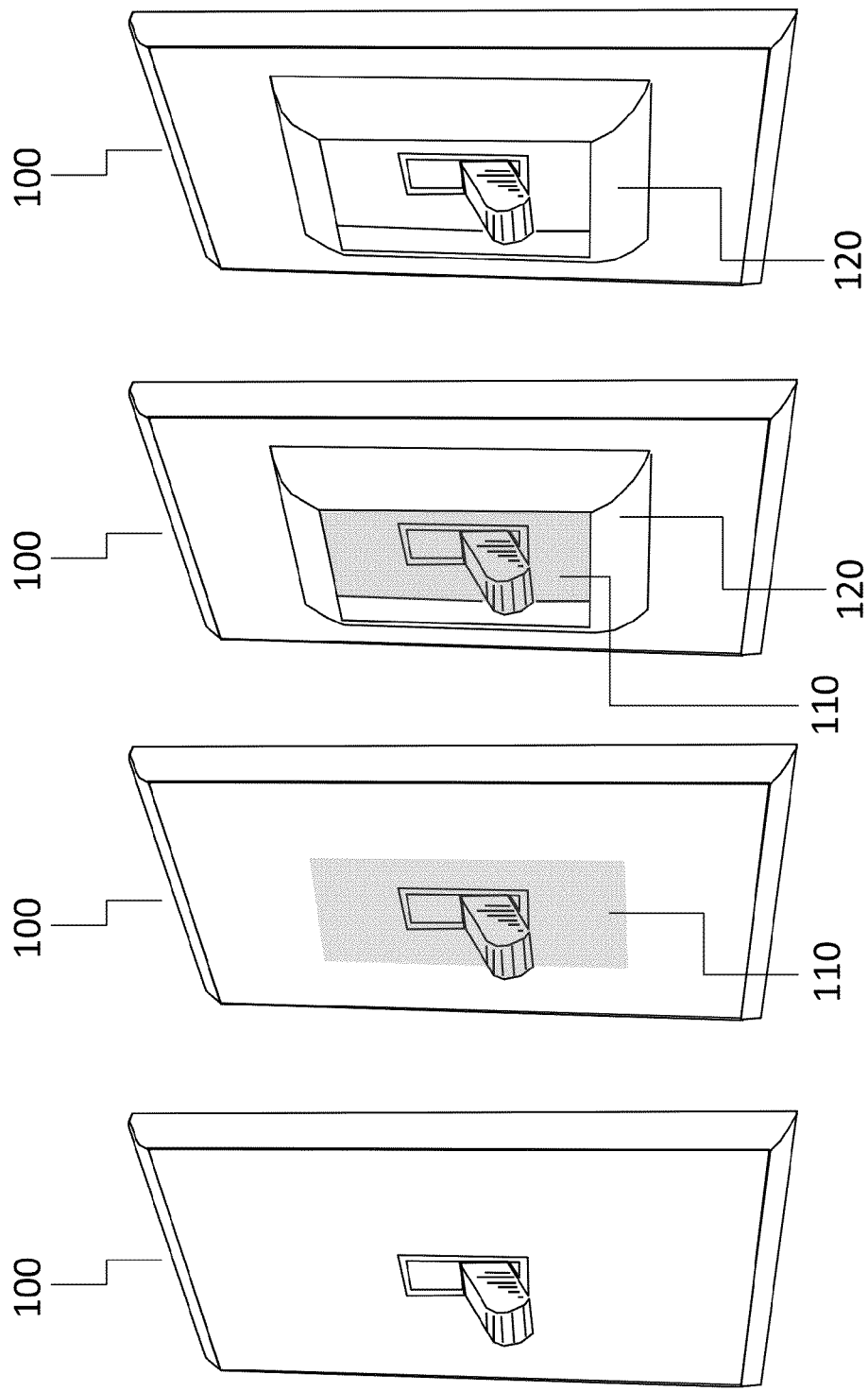
FIG. 1 is a perspective view of an illustrative example of the invented switch sanitizer, in accordance with the present invention, designed for use with a typical light switch.

Repeat use of a reference character in the present specification and drawings is intended to represent the same or analogous feature or element. Additionally, it is noted that the embodiments shown are not drawn to scale, and therefore are not intended to be limited by the relative size of the various components shown.

DETAILED DESCRIPTION OF INVENTION

The following description and other modifications and variations to the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the following description is by way of example only, and is not intended to limit the invention.

Generally, the present invention addresses the need for sanitization or decontamination of the contact areas of manual electronic switches by providing a localized source of germicidal electromagnetic radiation that is directed toward said contact surfaces. For example, the germicidal electromagnetic radiation can be directed via one or more of either mirrors or fiber optic elements or other means of changing the direction of electromagnetic radiation (EM) in an intentionally controlled manner.

The switches are designed specifically to expose the switch contact surfaces to the light source without appreciable exposure of humans or animals to the light source, having an angle of incidence equal to or exceeding 2° and equal to or less than 90° and exposing the contact surface(s) to be sanitized to more than 2,000 µW-s/cm² per treatment regime, while limiting exposure outside the region to be sanitized to less than 2,000 µW-s/cm² per interaction with said switch. This is accomplished through design of one or more of the factors of lighting angle, light shielding, light routing, or strategically turning the light on and off in a region local to the switch or switches. As such, a device is generally provided in one embodiment, to encapsulate the majority of the germicidal EM radiation produced to within the volume surrounded by said device such that minimal germicidal EM escapes from said volume. The device is open on at least one surface of said volume so as to enable manual access to the switch contact surface(s) so as to allow actuation of said switch. In order to enable said sanitization of said contact surfaces in an effective manner, the volume surrounded by the device is minimized such that the intensity of the EM germicidal source may be kept to a minimum thereby minimizing the intensity of any germicidal EM that may escape the device fixture that could possibly expose humans or animals to said germicidal EM. The amount of germicidal EM that escapes said device fixture is further minimized by design of the fixture as the fixture is designed to reflect the majority of the EM germicidal radiation emitted by the source of said EM germicidal radiation toward the switch contact surfaces or to within the volume surrounded by said device fixture.

The UV light source is preferably UV C, having a significant portion of light output in the region of 100 nm to 400 nm wavelength, preferably 200 to 300 nm wavelength, more preferably 250 nm to 260 nm wavelength. The light sources are local to the switch, with light outputs being no more than 6 inches from the switch, preferably no more than 1 to 3 inches from the switch and most preferably no more than 0.75 inches from the switch.

Additional means of reducing or eliminating unwanted germicidal EM radiation exposure of humans or animals may be incorporated into the invented device as well. Certain embodiments of this invention may also include functions that time the duration of illumination from the light source, or that turns off said illumination source when humans or animals are present, or when a finger, or the like, is in relatively close proximity (less than 6 inches away from said illumination source) to said device or similar, in order to ensure that the exposure of said contact surfaces to UV radiation is sufficient to sanitize the contact surface but exposure of humans and animals is further limited so as to minimize exposure of humans or animals to said radiation. Additional automation of the device to turn said illumination source on and off in the presence of humans or animals can further reduce or completely eliminate exposure of said humans or animals to said illumination source so as to further reduce or completely eliminate any exposure of said animals or humans to said illumination source.

Certain embodiments of this invention may include anti-reflective coatings on the switch contact surfaces, and or other portions of the interior surfaces of the surfaces that are surrounded by the positioning of said device in order to minimize escape of said radiation to the outside of said positioning. Using said device will enable use of a germicidal illumination source of minimum power, thus saving cost and energy, while being effective at sanitizing switch contact surfaces in a manner keeps said radiation localized to said switch contact surfaces in a manner that ensures non-hazardous exposure of humans or animals to said radiation.

In one embodiment, the switch sanitizer disclosed herein includes a germicidal UV light source mounted around an electrical or electronic switch and the area associated with touch points of said switch so as to sanitize said switch and said associated touch point areas. As such, the transference of active contamination species, known to be responsible for transmission of infectious disease, by way of sanitation can be reduced using germicidal UV light and/or the associated ozone generated by said germicidal UV light. The device is designed so as to enable effective sanitation of a switch device using a relatively low intensity germicidal UV light source, in local proximity to the switch and its associated contact surface areas. The light source is designed so as to direct the germicidal UV light toward said contact surface areas of said switch in a manner that is effective for sanitation of the switch and said contact surfaces, with minimal escape of the germicidal UV radiation to outside the device fixture so as to limit exposure of humans and animals to said germicidal UV radiation.

Additional means of reducing or eliminating unwanted germicidal EM radiation exposure of humans or animals may be incorporated into the invented device as well. Certain embodiments of this invention may also include functions that time the duration of illumination from the light source, or that turns off said illumination source when humans or animals are present, or when a finger, or the like, is in relatively close proximity (less than 6 inches away from said illumination source) to said device or similar, in order to ensure that the exposure of said contact surfaces to UV radiation is sufficient to sanitize the contact surface but exposure of humans and animals is further limited so as to minimize exposure of humans or animals to said radiation. Additional automation of the device to turn said illumination source on and off in the presence of humans or animals can further reduce or completely eliminate exposure of said humans or animals to said illumination source so as to further reduce or completely eliminate any exposure of said animals or humans to said illumination source, the light source having an angle of incidence between 2° and 90° and exposing the contact surface(s) to be sanitized to more than 2,000 µW-s/cm² per treatment regime, while limiting exposure outside the region to be sanitized to less than 2,000 µW-s/cm² per interaction with said switch.

While the disclosure is given with reference to a particular type switch sanitizing device, it is to be understood that the disclosure relates to all types of switch sanitizing devices that locally sanitize contact surfaces in a localized or surrounded volume, using germicidal EM radiation, while allowing manual access to said contact surface so as to allow manual actuation of an electrical or electronic switch, while minimizing the escape of said germicidal EM radiation to levels that are not hazardous to humans or animals. For example, the device may be useful for sanitizing electronic or electrical switches such as common light switches, elevator call buttons, elevator panel buttons, security panel buttons or switches, access panel buttons or switches, and the like and is not limited to type of switch or panel or display or the like. Additionally, the device is useful for sanitizing mechanical actuators such as toilet flush manual override switches or the like.

Referring to FIG. 1, an embodiment of the invented device 120 is mounted around the periphery of a common electrical light switch 100 so as to bound the periphery of the contact surface area 110 of said light switch 100 and to provide a means for illumination of said contact surface area 110 by germicidal UV radiation so as to keep contact area 110 sanitized.

Figure 2:
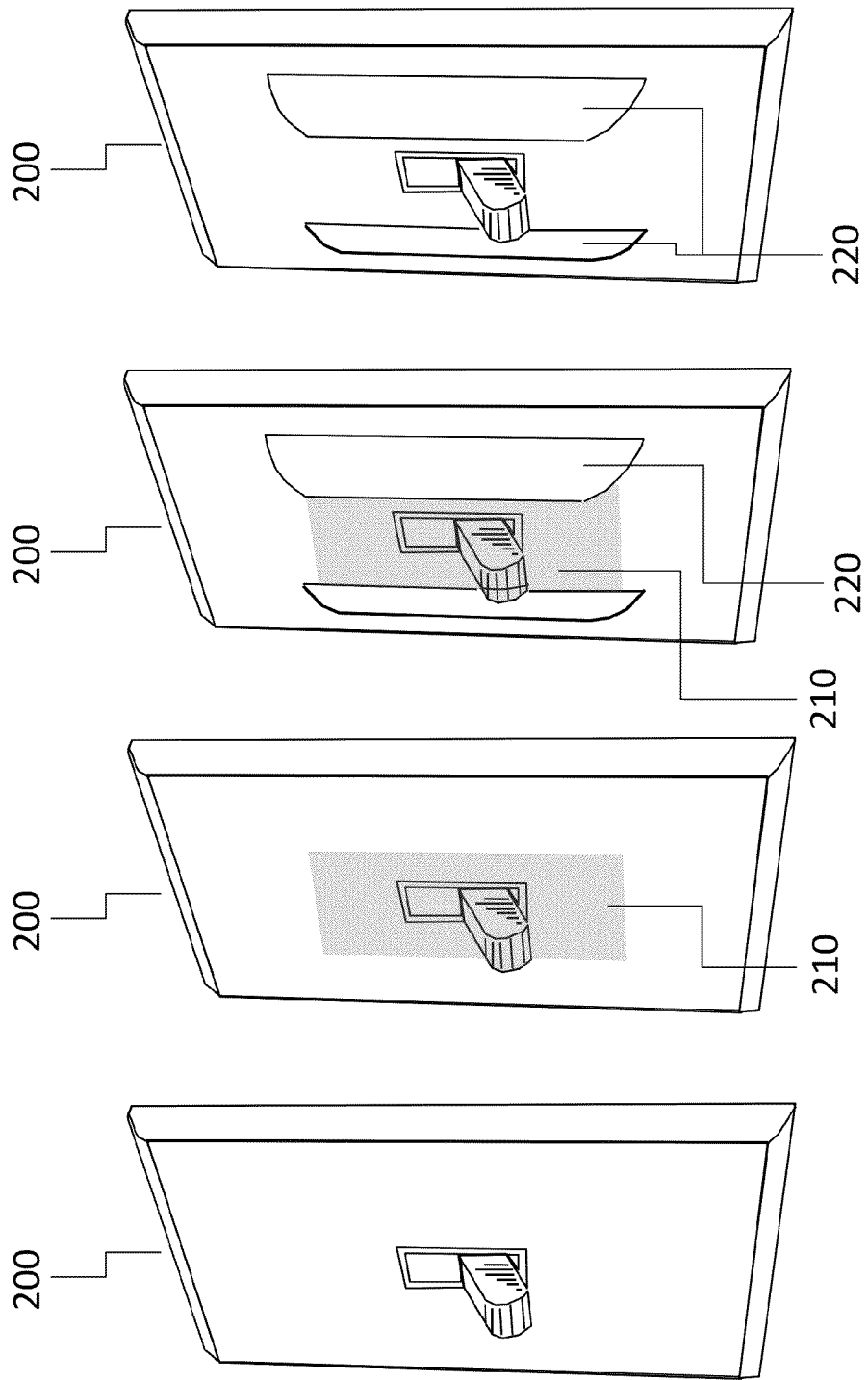
FIG. 2 is a perspective view of a second illustrative example of the invented switch sanitizer, in accordance with the present invention, designed for use with a typical light switch.

Referring to FIG. 2, a second embodiment of the invented device 220 is mounted around a portion of the periphery of a common electrical light switch 200 so as to bound a portion of the periphery of the contact surface area 210 of said light switch 200 and to provide a means for illumination of said contact surface area 210 by germicidal UV radiation so as to keep contact area 210 sanitized.

Figure 3:
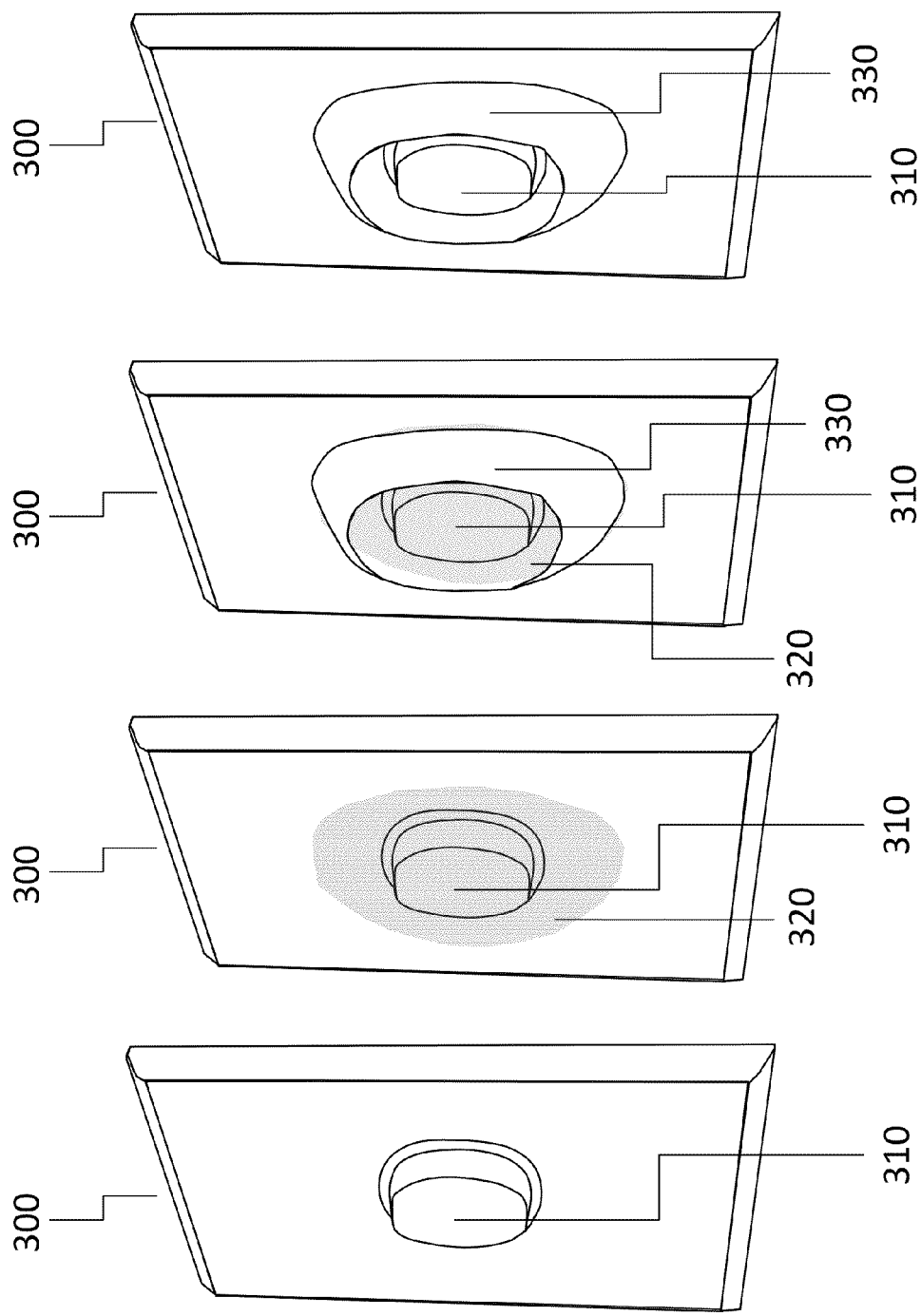

Referring to FIG. 3, a third embodiment of the invented device 330 is mounted around the periphery of a common push button type electrical or electronic switch 310 so as to bound a portion of the periphery of the contact surface area 320 of said push button type switch 310 and to provide a means for illumination of said contact surface area 320 by germicidal UV radiation so as to keep contact area 320 sanitized.

Figure 4:
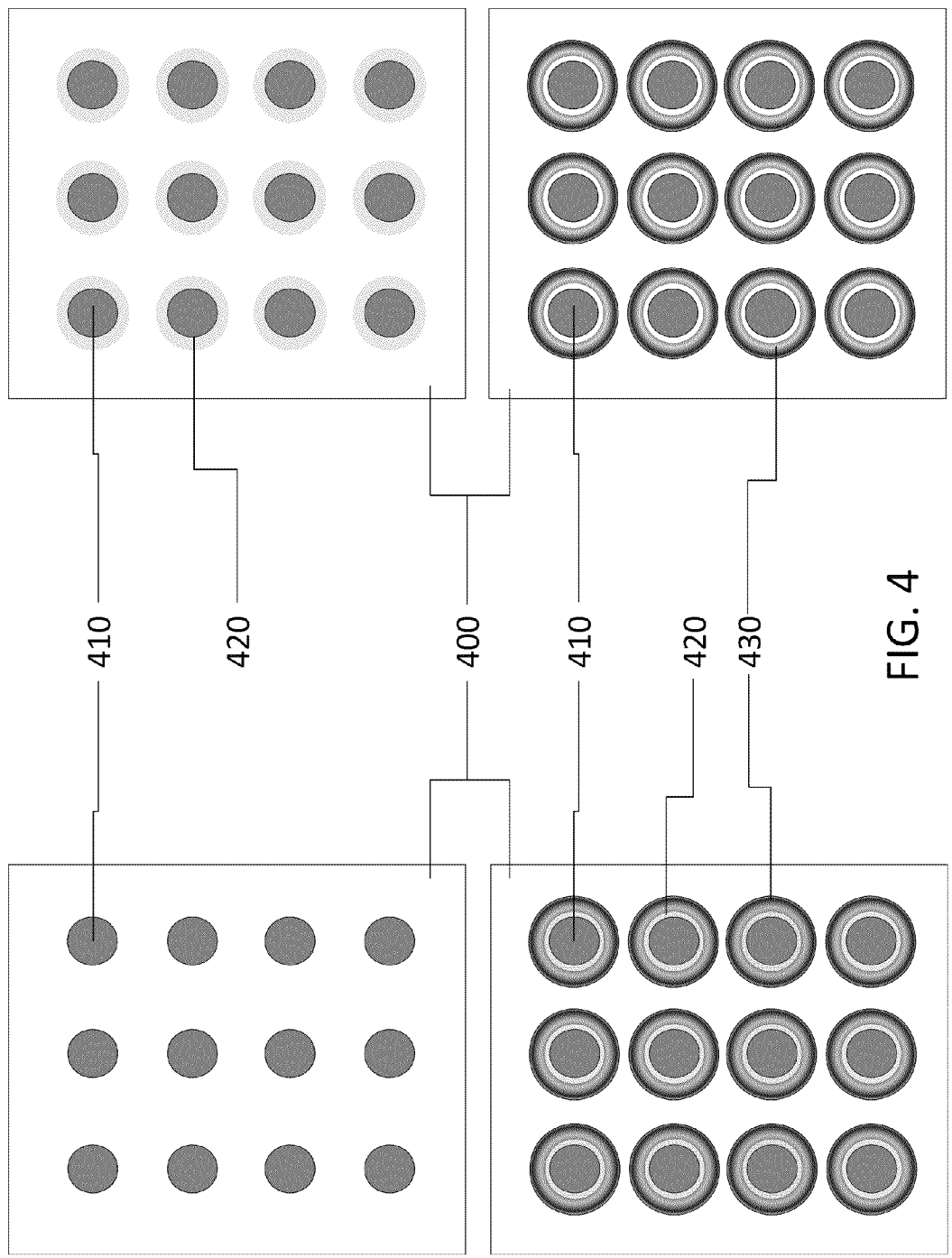

Referring to FIG. 4, a fourth embodiment of the invented device 430 is mounted around the periphery of each of a common push button type electrical or electronic switch 410 arranged in an array 400 or the like in a manner such as typically used in an elevator panel or the like. The device 430 is designed so as to bound all or a portion of the periphery of each of the contact surface areas 420 of said push button type switch array 400 in order to provide a means for illumination of each of said contact surface areas 420 by germicidal UV radiation so as to keep contact area 420 sanitized.

Figure 5:
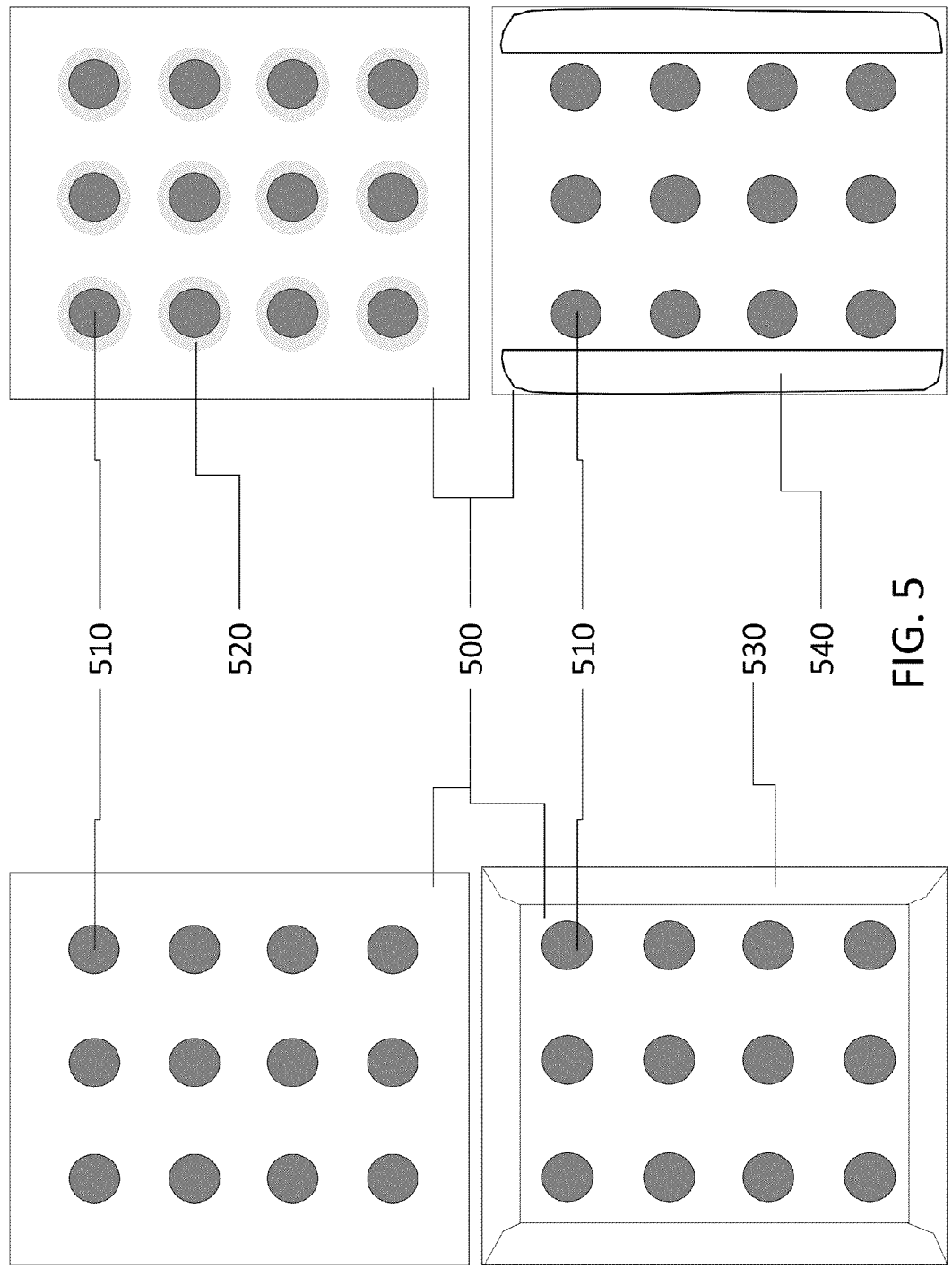

Referring to FIG. 5, a fifth 530 and a sixth 540 embodiment of the invented device are mounted around a portion of the periphery of an array of one or more common push button type electrical or electronic switches 510 arranged in an array 500 or the like in a manner such as typically used in an elevator panel or the like. Each of the embodiments 530 and 540 is designed so as to bound all or a portion of the periphery of at least an array of the contact surface areas 520 of said push button type switch array 500 in order to provide a means for illumination of said array 500 of said contact surface areas 520 by germicidal UV radiation so as to keep at least the contact areas 520 sanitized.

Figure 6:
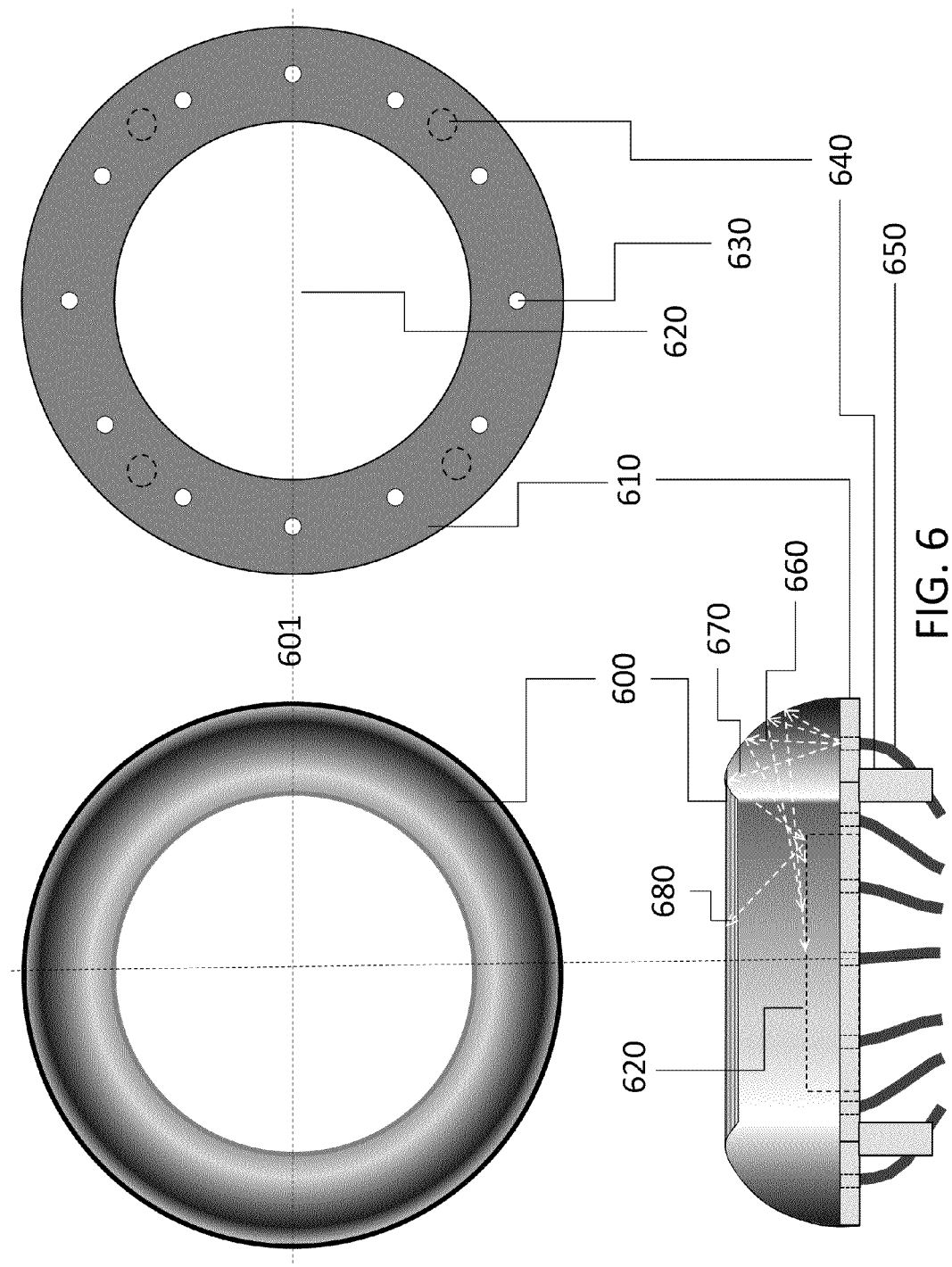
FIG. 6 is a sketch of an illustrative example of a switch sanitizer device showing a front view and a cross section view divided on line 601, in accordance with the present invention, utilizing a fiber optic type germicidal UV light source.

Referring to FIG. 6, an example of the germicidal UV light sanitizing device utilizing UV C capable fiber optic germicidal light sources and consistent with the invention 600, is shown. The upper left view is the appearance of the device from the top as installed. The upper right view is the appearance of the base fixture 610 of the device 600, showing a series of 12 holes 630 to enable feed through of the fiber optic light sources 650. The bottom left view is a cross section view along line 601 showing the outer fixture 600 being affixed to the base 610 via a fixturing means such as glue, clips, screws, clamps or the like as would be understood by a person of skill in the art. A means 640 for mounting the device to a panel such as those illustrated in FIG. 3 (300) or FIG. 4 (400) is illustrated. The device is designed so as to surround a button type switch such as FIG. 3 (310) or FIG. 4 (410) having a hole 620 to surround the volume that the button type switch and associated touch areas 620 comprise. The UV C capable fiber elements 650 are mounted in feed-throughs 630 in a manner that allows germicidal UV C light to beneficially illuminate the inner surface of fixture 600 such that the germicidal EM is reflected beneficially toward said switch contact areas 620 in a manner that sanitizes the said surfaces 620. The transmitted germicidal UV C EM is directed 660 toward the interior surface of the outer fixture 600 such that said EM is directed toward the contact surfaces 620 with minimal emission of said EM to the exterior of the device 600 as indicated by EM ray 680. By minimizing the angle of reflection of EM 670 such that minimal EM 680 escapes the fixture 600, a maximum amount of EM 670 is made available to sanitize the contact areas 620 and a minimum amount of said EM 680 escapes the fixture 600, reducing the exposure of any humans or animals outside the fixture to a non-deleterious amount.

Additional means of reducing or eliminating unwanted germicidal EM radiation exposure of humans or animals may be incorporated into the current embodiment as well. The invention may also include functions that time the duration of illumination from the light source, or that turns off said illumination source when humans or animals are present, or when a finger, or the like, is in relatively close proximity (less than 6 inches away from said illumination source) to said device or similar, in order to ensure that the exposure of said contact surfaces 620 to said EM is sufficient to sanitize the contact surface but exposure of humans and animals is further limited so as to minimize exposure of humans or animals to said radiation 680. Additional automation of the device to turn said illumination source on and off in the presence of humans or animals can further reduce or completely eliminate exposure of said humans or animals to said illumination source 650 so as to further reduce or completely eliminate any exposure of said animals or humans to said illumination source 650. Additionally, this invention may include anti-reflective coatings on the contact area 620 in order to minimize escape of said radiation to the outside of said fixturing. Using said device will enable use of an EM source 650 of minimum power, thus saving cost and energy, while being effective at sanitizing switch contact surfaces 620 in a manner keeps said radiation 670 localized to said switch contact surfaces 620 in a manner that ensures non-hazardous exposure levels of humans or animals to said radiation 680. Other light sources may also be used in order to provide additional functionalities such visible light LEDs so as to provide optical illumination or the like.

Figure 7:
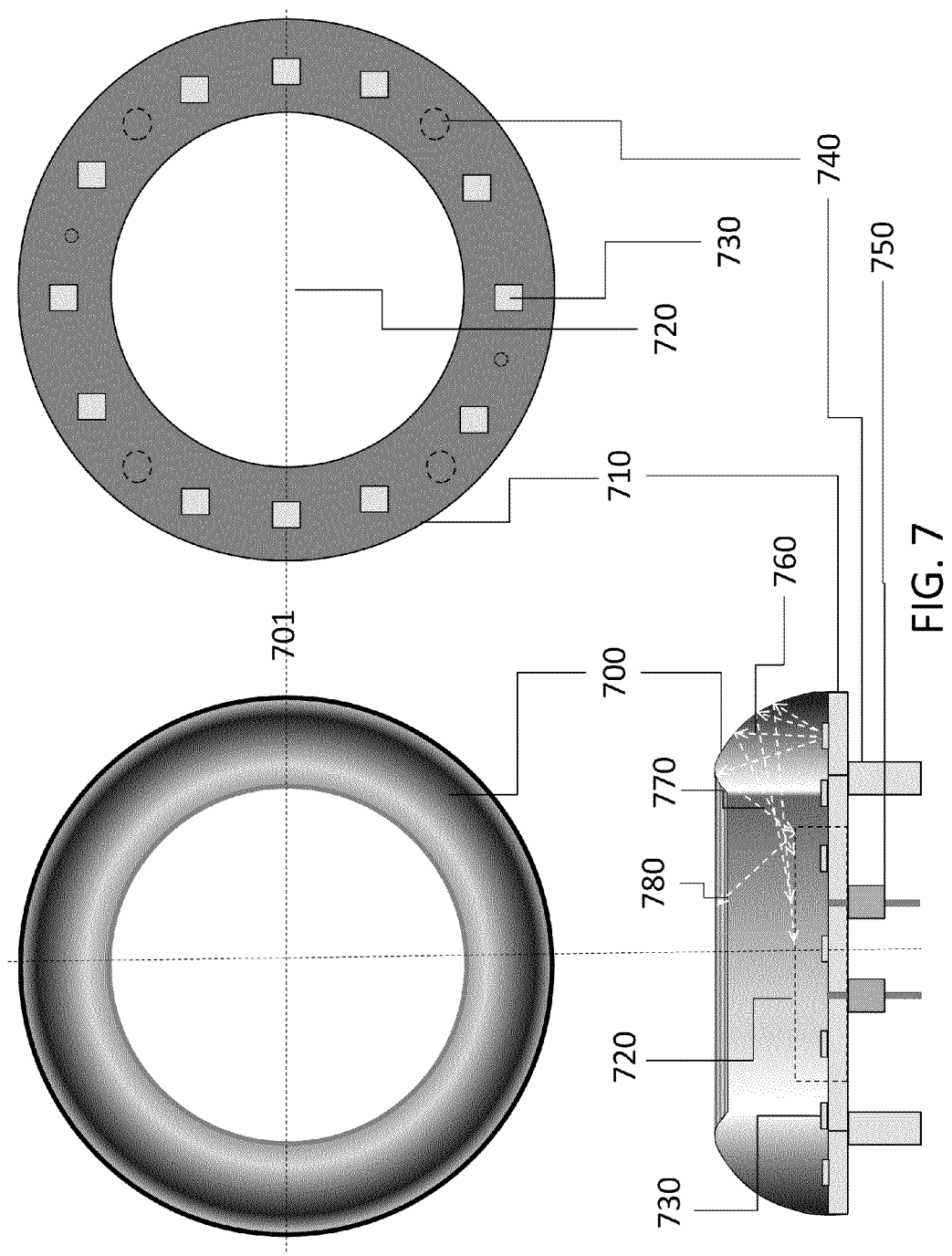
FIG. 7 is a sketch of a second illustrative example of a switch sanitizer device showing a front view and a cross section view divided on line 701, in accordance with the present invention, utilizing a chip type light emitting diode type germicidal UV light source.

Referring to FIG. 7 an example of the germicidal UV light sanitizing device utilizing germicidal UV C chip type light emitting diodes (LEDs) EM light sources and consistent with the invention 700, is shown. The upper left view is the appearance of the device from the top as installed. The upper right view is the appearance of the base fixture 710 of the device 700, showing a series of 12 LEDs 730 mounted physically to base 710 to provide said EM light sources 730. The bottom left view is a cross section view along line 701 showing the outer fixture 700 being affixed to the base 710 via a fixturing means such as glue, clips, screws, clamps or the like as would be understood by a person of skill in the art. A means 740 for mounting the device to a panel such as those illustrated in FIG. 3 (300) or FIG. 4 (400) is illustrated. The device is designed so as to surround a button type switch such as FIG. 3 (310) or FIG. 4 (410) having a hole 720 in its central region so as to surround the volume that the button type switch and associated touch areas 720 comprise. The UV C capable LEDs 730 are mounted to base 710 in a manner that allows germicidal UV C light 760 to beneficially illuminate the inner surface of fixture 700 such that the germicidal EM is reflected beneficially toward said switch contact areas 720 in a manner that sanitizes the said surfaces 720. Power to the LEDs 730 is provided to the LEDs by an electrical transmission means 750, such as a feed through device or that like as would be well understood by a person of skill in the art. The electrical transmission means may include additional circuitry, as would be understood by one of skill in the art, so as to distribute electricity to each of the LEDs 730 so as to enable appropriate illumination of all of the LEDs 730. The transmitted germicidal UV C EM 760 is directed 770 toward the interior surface of the outer fixture 700 such that said EM 760 is directed toward the contact surfaces 720 with minimal emission of said EM to the exterior of the device 700 as indicated by EM ray 780. By minimizing the angle of reflection of EM 770 such that minimal EM 780 escapes the fixture 700, a maximum amount of EM 760 and 770 is made available to sanitize the contact areas 720 and a minimum amount of said EM 780 escapes the fixture 700, reducing the exposure of any humans or animals outside the fixture to a non-deleterious amount.

Additional means of reducing or eliminating unwanted germicidal EM radiation exposure of humans or animals may be incorporated into the current embodiment as well. The invention may also include functions that time the duration of illumination from the light source, or that turns off said illumination source when humans or animals are present, or when a finger, or the like, is in relatively close proximity (less than 6 inches away from said illumination source) to said device or similar, in order to ensure that the exposure of said contact surfaces 720 to said EM is sufficient to sanitize the contact surface but exposure of humans and animals is further limited so as to minimize exposure of humans or animals to said radiation 780. Additional automation of the device to turn said illumination source on and off in the presence of humans or animals can further reduce or completely eliminate exposure of said humans or animals to said illumination source 730 so as to further reduce or completely eliminate any exposure of said animals or humans to said illumination source 730. Additionally, this invention may include anti-reflective coatings on the contact area 720 in order to minimize escape of said radiation to the outside of said fixturing. Using said device will enable use of an EM source 730 of minimum power, thus saving cost and energy, while being effective at sanitizing switch contact surfaces 720 in a manner keeps said radiation 760 and 770 localized to said switch contact surfaces 720 in a manner that ensures non-hazardous exposure levels of humans or animals to said radiation 780. Other light sources may also be used in order to provide additional functionalities such visible light LEDs so as to provide optical illumination or the like.

Figure 8:
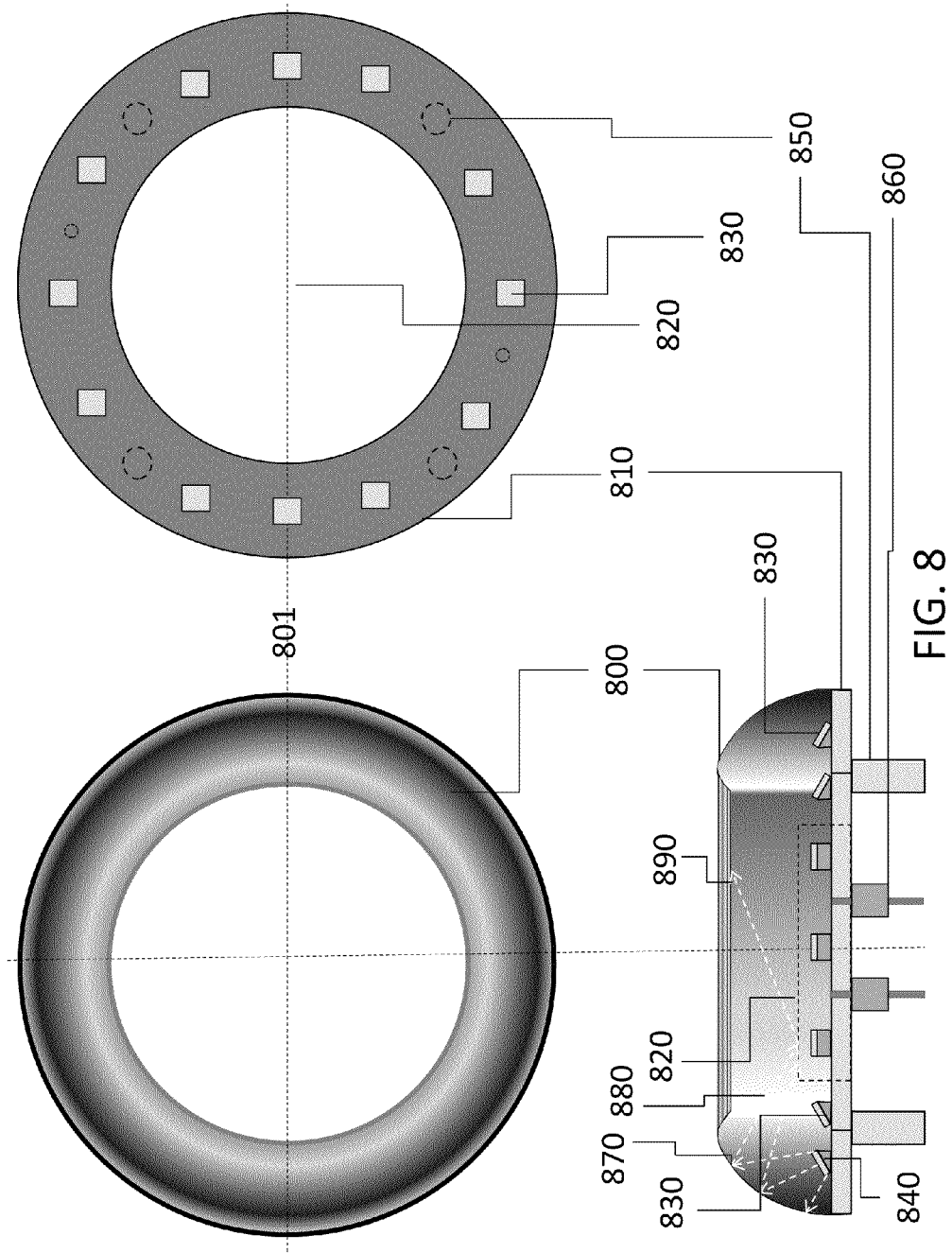
FIG. 8 is a sketch of a third illustrative example of a switch sanitizer device showing a front view and a cross section view divided on line 801, in accordance with the present invention, utilizing an angled chip type light emitting diode type germicidal UV light source.

Referring to FIG. 8 an example of the germicidal UV light sanitizing device utilizing angle adjusted germicidal UV C chip type light emitting diodes (LEDs) EM light sources and consistent with the invention 800, is shown. The upper left view is the appearance of the device from the top as installed. The upper right view is the appearance of the base fixture 810 of the device 800, showing a series of 12 LEDs 830 mounted physically to and angle adjustment device 840 which is in turn physically mounted to base 810 to provide said EM light sources 830. The bottom left view is a cross section view along line 801 showing the outer fixture 800 being affixed to the base 810 via a fixturing means such as glue, clips, screws, clamps or the like as would be understood by a person of skill in the art. A means 850 for mounting the device to a panel such as those illustrated in FIG. 3 (300) or FIG. 4 (400) is illustrated. The device is designed so as to surround a button type switch such as FIG. 3 (310) or FIG. 4 (410) having a hole 820 in its central region so as to surround the volume that the button type switch and associated touch areas 820 comprise. The UV C capable LEDs 830 are mounted to base 810 via angle adjustment devices 840 in a manner that allows germicidal UV C light 870 to beneficially illuminate 880 the inner surface of fixture 800 such that the germicidal EM is reflected beneficially toward said switch contact areas 820 in a manner that sanitizes the said surfaces 820. Power to the LEDs 830 is provided by the LEDs by an electrical transmission means 860, such as a feed through device or that like as would be well understood by a person of skill in the art. The electrical transmission means may include additional circuitry so as to distribute electricity to each of the LEDs 830 so as to enable appropriate illumination of all of the LEDs 830 as would be understood by one of skill in the art. The transmitted germicidal UV C EM 870 is directed toward the interior surface of the outer fixture 800 such that said EM 870 is directed toward 880 the contact surfaces 820 with minimal emission 890 of said EM to the exterior of the device 800 as indicated by EM ray 890. By minimizing the angle of reflection of EM 880 such that minimal EM 890 escapes the fixture 800, a maximum amount of EM 870 and 880 is made available to sanitize the contact areas 820 and a minimum amount of said EM 890 escapes the fixture 800, reducing the exposure of any humans or animals outside the fixture to a non-deleterious amount.

Additional means of reducing or eliminating unwanted germicidal EM radiation exposure of humans or animals may be incorporated into the current embodiment as well. The invention may also include functions that time the duration of illumination from the light source, or that turns off said illumination source when humans or animals are present, or when a finger, or the like, is in relatively close proximity (less than 6 inches away from said illumination source) to said device or similar, in order to ensure that the exposure of said contact surfaces 820 to said EM is sufficient to sanitize the contact surface but exposure of humans and animals is further limited so as to minimize exposure of humans or animals to said radiation 890. Additional automation of the device to turn said illumination source on and off in the presence of humans or animals can further reduce or completely eliminate exposure of said humans or animals to said illumination source 830 so as to further reduce or completely eliminate any exposure of said animals or humans to said illumination source 830. Additionally, this invention may include anti-reflective coatings on the contact area 820 in order to minimize escape of said radiation to the outside of said fixturing. Using said device will enable use of an EM source 830 of minimum power or intensity, thus saving cost and energy, while being effective at sanitizing switch contact surfaces 820 in a manner keeps said radiation 870 localized to said switch contact surfaces 820 in a manner that ensures non-hazardous exposure levels of humans or animals to said radiation 890. Other light sources may also be used in order to provide additional functionalities such visible light LEDs so as to provide optical illumination or the like.

Figure 9:
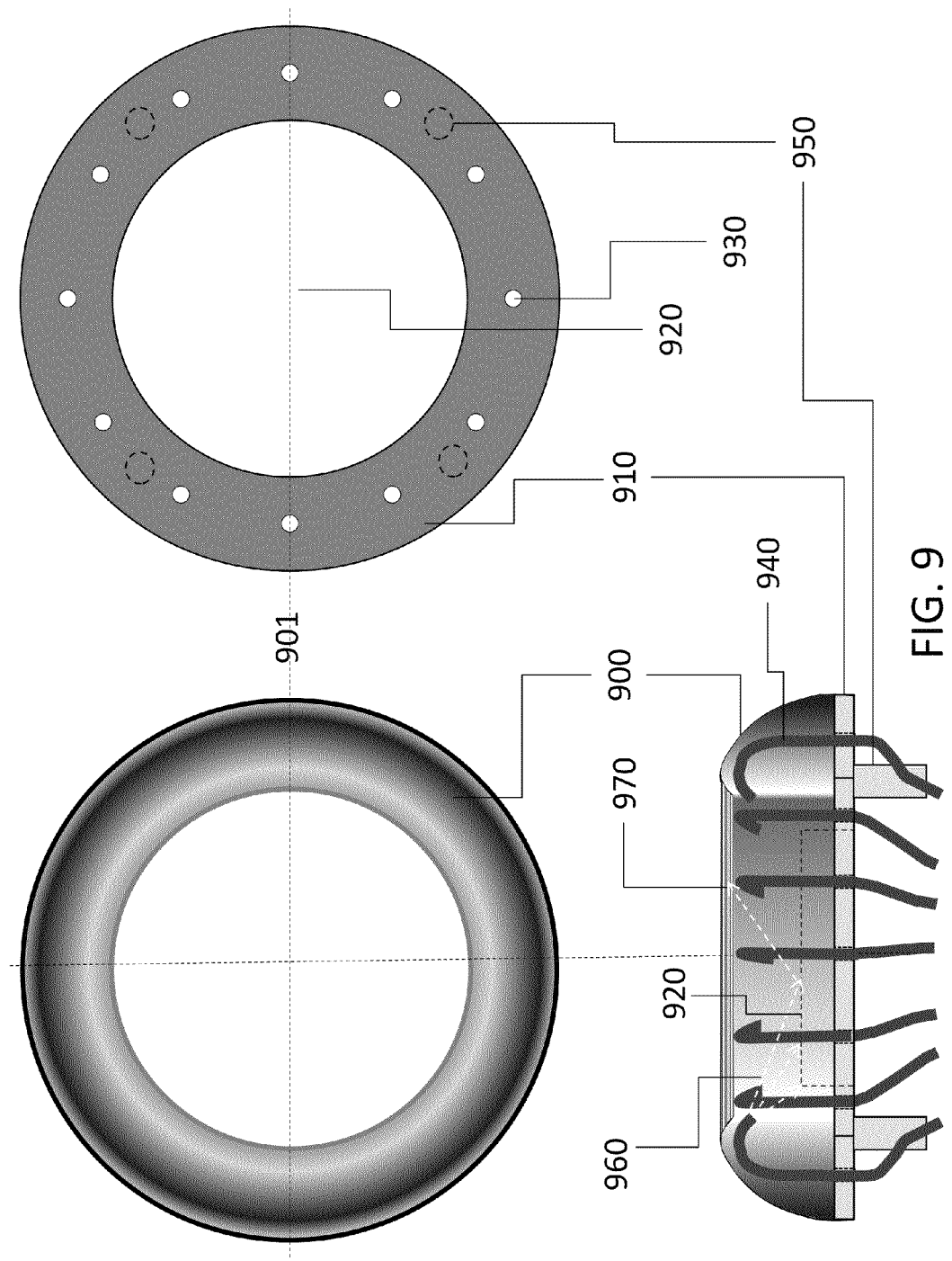
FIG. 9 is a sketch of a fourth illustrative example of a switch sanitizer device showing a front view and a cross section view divided on line 901, in accordance with the present invention, utilizing an angled fiber optic type germicidal UV light source.

Referring to FIG. 9 an example of the germicidal UV light sanitizing device utilizing angle adjusted germicidal UV C capable optic fiber as the EM sources and consistent with the invention 900, is shown. The upper left view is the appearance of the device from the top as installed. The upper right view is the appearance of the base fixture 910 of the device 900, showing a series of 12 holes 930 in base 910 to enable feed through of said EM fiber transmission elements 940 through said base 910. Said optic fiber elements 940 are arranged so as to direct said EM directly at the switch contact surfaces 920. The source of said EM is not illustrated, but each fiber 940 is illuminated appropriately by means that are easily accomplished by a person of skill in the art. The bottom left view is a cross section view along line 901 showing the outer fixture 900 being affixed to the base 810 via a fixturing means such as glue, clips, screws, clamps or the like as would be understood by a person of skill in the art. A means 950 for mounting the device to a panel such as those illustrated in FIG. 3 (300) or FIG. 4 (400) is illustrated. The device is designed so as to surround a button type switch such as FIG. 3 (310) or FIG. 4 (410) having a hole 920 in its central region so as to surround the volume that the button type switch and associated touch areas 920 comprise. The fiber optic elements 940 are mounted within the fixture 900 in a manner that allows germicidal UV C light 960 to beneficially illuminate 960 the inner surface of fixture 900 and the contact areas 920 such that the germicidal EM is directed or reflected beneficially toward said switch contact areas 920 in a manner that sanitizes the said surfaces 920. Provision of illumination to the fiber optic elements 940, while not illustrated, is well understood by a person of skill in the art. The transmitted germicidal UV C EM 960 is directed toward the contact areas 920 such that said EM 960 is directed toward the contact surfaces 920 with minimal emission 970 of said EM to the exterior of the device 900 as indicated by EM ray 970. By minimizing the angle of reflection of EM 960 such that minimal EM 970 escapes the fixture 900, a maximum amount of EM 960 is made available to sanitize the contact areas 920 and a minimum amount of said EM 970 escapes the fixture 900, reducing the exposure of any humans or animals outside the fixture to a non-deleterious amount.

Additional means of reducing or eliminating unwanted germicidal EM radiation exposure of humans or animals may be incorporated into the current embodiment as well. The invention may also include functions that time the duration of illumination from the light source, or that turns off said illumination source when humans or animals are present, or when a finger, or the like, is in relatively close proximity (less than 6 inches away from said illumination source) to said device or similar, in order to ensure that the exposure of said contact surfaces 920 to said EM is sufficient to sanitize the contact surface but exposure of humans and animals is further limited so as to minimize exposure of humans or animals to said radiation 970. Additional automation of the device to turn said illumination source on and off in the presence of humans or animals can further reduce or completely eliminate exposure of said humans or animals to said illumination source 940 so as to further reduce or completely eliminate any exposure of said animals or humans to said illumination source 940. Additionally, this invention may include anti-reflective coatings on the contact area 920 in order to minimize escape of said radiation to the outside of said fixturing. Using said device will enable use of an EM source 920 of minimum power or intensity, thus saving cost and energy, while being effective at sanitizing switch contact surfaces 920 in a manner keeps said radiation 960 localized to said switch contact surfaces 920 in a manner that ensures non-hazardous exposure levels of humans or animals to said radiation 970. Other light sources may also be used in order to provide additional functionalities such visible light LEDs so as to provide optical illumination or the like.

Figure 10:
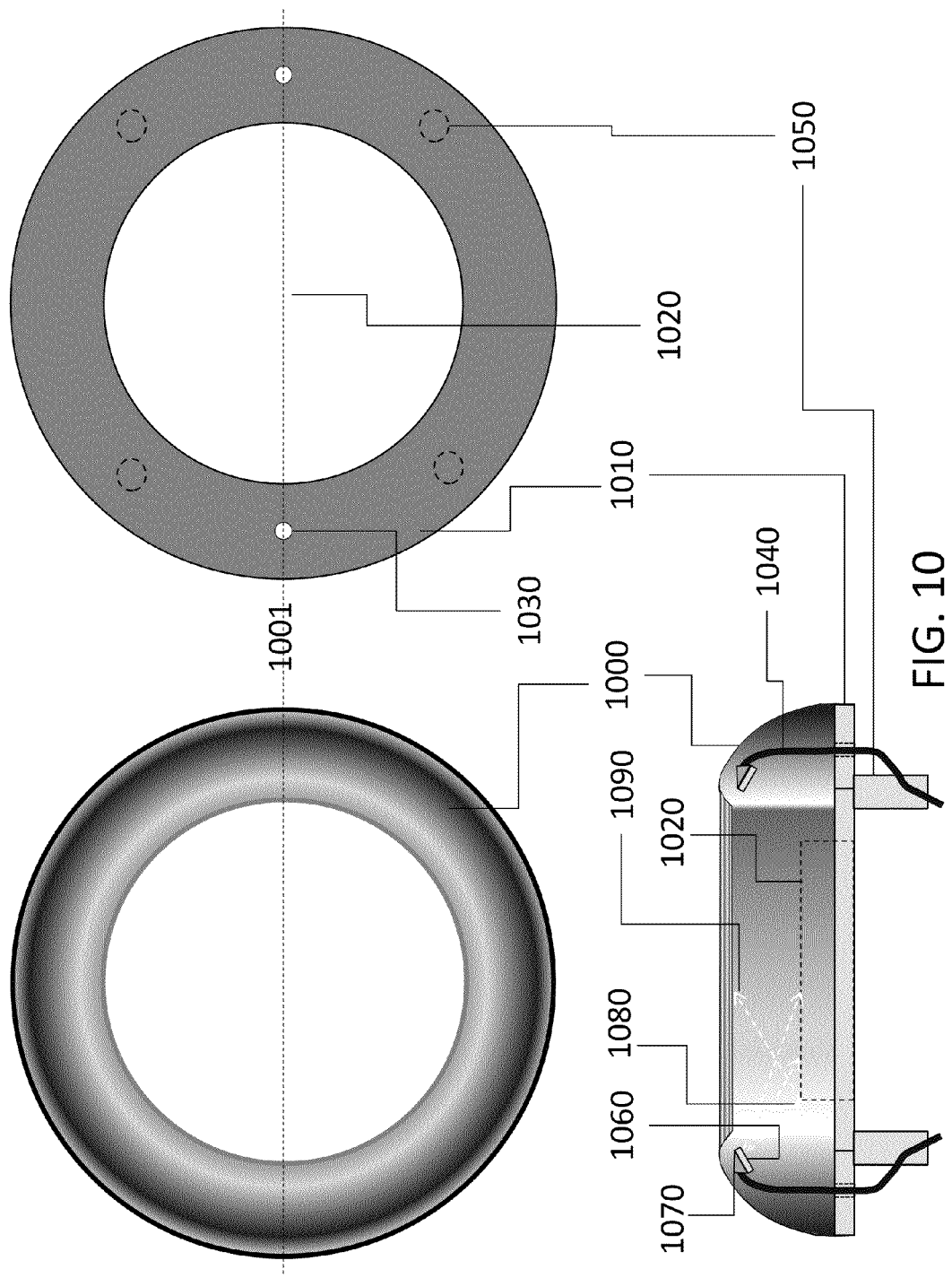
FIG. 10 is a sketch of a fifth illustrative example of a switch sanitizer device showing a front view and a cross section view divided on line 901, in accordance with the present invention, utilizing an angled chip type light emitting diode type germicidal UV light source.

Referring to FIG. 10 an example of the germicidal UV light sanitizing device utilizing angle adjusted germicidal UV C chip type light emitting diodes (LEDs) EM light sources and consistent with the invention 1000 is shown. The upper left view is the appearance of the device from the top as installed. The upper right view is the appearance of the base fixture 1010 of the device 1000, showing a series of 2 LEDs 1060 each mounted physically to an angle adjustment device 1070 which is in turn physically mounted to fixture 1000 to provide said EM light sources 1080. The LED devices 1060 are powered through electrical means 1040 that are comprised of an electrically conducting wire or the like as would be understood by one of skill in the art. The bottom left view is a cross section view along line 1001 showing the outer fixture 1000 being affixed to the base 1010 via a fixturing means such as glue, clips, screws, clamps or the like as would be understood by a person of skill in the art. A means 1050 for mounting the device to a panel such as those illustrated in FIG. 3 (300) or FIG. 4 (400) is illustrated. The device is designed so as to surround a button type switch such as FIG. 3 (310) or FIG. 4 (410) having a hole 1020 in its central region so as to surround the volume that the button type switch and associated touch areas 1020 comprise. The UV C capable LEDs 1060 are mounted to angle adjustment devices 1070 which is in turn physically mounted to the fixture 1000 or other supporting means in a manner that allows germicidal UV C light 1080 to beneficially illuminate the contact surfaces 1020 as well as the inner surface of fixture 1000 such that the germicidal EM is reflected beneficially toward said switch contact areas 1020 in a manner that sanitizes the said surfaces 1020. Power to the LEDs 1060 is provided to the LEDs by an electrical transmission means 1040, such as a wire or the like as would be well understood by a person of skill in the art. The electrical transmission means may include additional circuitry so as to distribute electricity to each of the LEDs 1060 so as to enable appropriate illumination of all of the LEDs 1060 as would be understood by one of skill in the art. The transmitted germicidal UV C EM 1080 is directed toward the interior surface of the outer fixture 1000 such that said EM 1080 is directed toward the contact surfaces 1020 with minimal emission 1090 of said EM to the exterior of the device 1000 as indicated by EM ray 1090. By minimizing the angle of reflection of EM 1080 such that minimal EM 1090 escapes the fixture 1000, a maximum amount of EM 1080 is made available to sanitize the contact areas 1020 and a minimum amount of said EM 1090 escapes the fixture 1000, reducing the exposure of any humans or animals outside the fixture to a non-deleterious amount.

Additional means of reducing or eliminating unwanted germicidal EM radiation exposure of humans or animals may be incorporated into the current embodiment as well. The invention may also include functions that time the duration of illumination from the light source, or that turns off said illumination source when humans or animals are present, or when a finger, or the like, is in relatively close proximity (less than 6 inches away from said illumination source) to said device or similar, in order to ensure that the exposure of said contact surfaces 1020 to said EM is sufficient to sanitize the contact surface but exposure of humans and animals is further limited so as to minimize exposure of humans or animals to said radiation 1090. Additional automation of the device to turn said illumination source on and off in the presence of humans or animals can further reduce or completely eliminate exposure of said humans or animals to said illumination source 1060 so as to further reduce or completely eliminate any exposure of said animals or humans to said illumination source 1060. Additionally, this invention may include anti-reflective coatings on the contact area 1020 in order to minimize escape of said radiation to the outside of said fixturing. Using said device will enable use of an EM source 1060 of minimum power or intensity, thus saving cost and energy, while being effective at sanitizing switch contact surfaces 1020 in a manner keeps said radiation 1080 localized to said switch contact surfaces 1020 in a manner that ensures non-hazardous exposure levels of humans or animals to said radiation 1090. Other light sources may also be used in order to provide additional functionalities such visible light LEDs so as to provide optical illumination or the like.

Another exemplary embodiment of a switch sanitizing device 5 is generally shown in FIGS. 11-14. The device 5 includes a light switch 10 extending through a switch aperture, light guide, lens, waveguide, light pipe or the like 7 defined by the plate 6. The light switch 10 defines a first contact surface area 12 and a second contact surface area 13. In use, one applies force to the second contact surface area 13 (e.g., via a finger) to move the light switch 10 from an off-position to an on-position, and presses on the first contact surface area 12 to move the light switch 10 from the on-position to the off-position. Referring to FIG. 13A, the light switch 10 is shown in the on-position, with a corresponding general electric diagram is shown in FIG. 14A. Conversely, referring to FIG. 13B, the light switch 10 is shown in the off-position, with a corresponding general electric diagram is shown in FIG. 14B. For example, plate 6 and light switch 10 can be similar to convention light switch devices typically available.

A first sanitizing light 20 and a second sanitizing light 30 are positioned on plate 6 at opposite sides of the switch 10. Generally, the first and second sanitizing lights 20, 30 are configured to direct UV radiation (e.g., a UV C radiation) toward the first contact surface area 12 and the second contact surface area 13, respectively either directly, or through an aperture or light guide, lens, waveguide, light pipe or the like. Each of the first and second sanitizing lights 20, 30 are generally configured to direct the UV radiation toward the respective contact surface area 12, 13 while minimizing the amount of UV radiation that strays from the device 10. That is, the first and second sanitizing lights 20, 30 are, in one embodiment, positioned and configured such that about 50% or greater of the UV electromagnetic radiation is directed toward the respective contact surface area 12, 13, such as about 60% or greater, preferably about 70% or greater, more preferably about 80% or greater. In one particular embodiment, the first and second sanitizing lights 20, 30 are, in one embodiment, positioned and configured such that about 90% or greater of the UV electromagnetic radiation is directed toward the respective contact surface area 12, 13, such as about 95% or greater, preferably about 98% or greater, more preferably about 99% or greater (e.g., about 99.5% or greater) as the light source is configured to have an angle of incidence between 2° and 90° and exposing the contact surface(s) to be sanitized to more than 2,000 $\mu W\text{-s/cm}^2$ per treatment regime, while limiting exposure outside the region to be sanitized to less than 2,000 $\mu W\text{-s/cm}^2$ per interaction with said switch.

As shown in FIG. 12, the first sanitizing light 20 generally includes a first light source 22 that receives power through a first wire 24. A first housing 26 is positioned on the plate 6, and defines an internal reflective surface 28 therein. The first light source 22 generates UV electromagnetic radiation (represented by arrows 9) that is directed through a first aperture in the plate 6 and into the housing 26. In turn, the internal reflective surface 28 of the first housing 26 redirects the UV electromagnetic radiation toward the first contact surface 12 (FIG. 13A). Thus, the amount of UV electromagnetic radiation that escapes the device 10 is minimized as the light source having an angle of incidence between 2° and 90° and exposing the contact surface(s) to be sanitized to more than 2,000 $\mu W\text{-s/cm}^2$ per treatment regime, while limiting exposure outside the region to be sanitized to less than 2,000 $\mu W\text{-s/cm}^2$ per interaction with said switch.

Similarly, the second sanitizing light 30 generally includes a second light source 32 that receives power through second wire 34. A second housing 36 is positioned on the plate 6, and defines an internal reflective surface 38 therein. The second light source 32 generates UV electromagnetic radiation (represented by arrows 9) that is directed either directly or through a second aperture, light guide, lens, waveguide, light pipe or the like in the plate 6 and into the second housing 36. In turn, the internal reflective surface 38 of the second housing 36 redirects the UV electromagnetic radiation toward the second contact surface 13 (FIG. 13B). Thus, the amount of UV electromagnetic radiation that escapes the device 10 is minimized.

As shown in FIGS. 13A and 14A, when the light switch is in the on-position, the light 40 and the first sanitizing light 20 are electrically connected to the power source 50 such that both the light 40 and the first sanitizing light 20 powered. Conversely, when in the on-position, the second sanitizing light 30 is electrically isolated from the power source 50, and does not receive power. Thus, in the on-position, the switch 10 is closest to the first sanitizing light 20, with the first contact surface area 12 to be most likely contacted by a user (i.e., to apply a force to move the switch 10 to the off-position). Thus, the switch 10 is being sanitized by the first sanitizing light 20 in the area most likely to be contacted by a user (i.e., the first contact surface area 12), but not in any other area. Additionally, due to the angle of the switch 10, the UV electromagnetic radiation 9 that contacts the first contact surface area 12 is not likely to reflect out of the device 10 but instead toward the plate 6. In certain embodiments, an anti-reflective coating can be included on the first contact surface area 12 to further inhibit the UV electromagnetic radiation 9 from escaping the device 10.

Conversely, as shown in FIGS. 13B and 14B, when the light switch is in the off-position, the light 40 and the first sanitizing light 20 are electrically isolated from the power source 50 such that both the light 40 and the first sanitizing light 20 do not receive power. Conversely, when in the off-position, the second sanitizing light 30 is electrically connected to the power source 50 to receive power. Thus, in the off-position, the switch 10 is closest to the second sanitizing light 30, with the second contact surface area 13 to be most likely contacted by a user (i.e., to apply a force to move the switch 10 to the on-position). Thus, the switch 10 is being sanitized by the second sanitizing light 20 in the area most likely to be contacted by a user (i.e., the second contact surface area 13), but not in any other area. Additionally, due to the angle of the switch 10, the UV electromagnetic radiation 9 that contacts the second contact surface area 13 is not likely to reflect out of the device 10 but instead toward the plate 6. In certain embodiments, an anti-reflective coating can be included on the second contact surface area 12 to further inhibit the UV electromagnetic radiation 9 from escaping the device 10.

The light switch 10 generally controls the power to the light 40, the first sanitizing light 20, and the second sanitizing light 30 through the electrical switch 14, which is diagramed in FIGS. 14A and 14B.

The housing 26, 36 of each of the sanitizing lights 20, 30 is generally opaque so as to block substantially all of the UV electromagnetic radiation 9 from transmitting there through. Thus, the housing 26, 36 inhibits the UV electromagnetic radiation 9 from escaping the device 10. For example, the housing 26, 36 can be constructed from a plastic, metal, rubber, or other suitable material.

The reflective surface 28, 38 in the respective housing 26, 36 is generally reflective to the wavelengths emitted by the light sources 22, 32 (e.g., UV C electromagnetic radiation). As shown, each housing 26, 36 has a conical shape and defines an open end 27, 37, respectively, that faces to the light switch 12. As such, the UV electromagnetic radiation can be collected within the housing and generally concentrated in a direction toward the light switch 12 with minimal or virtually no UV electromagnetic radiation escaping the device. However, any suitable shape can be utilize for the housing 26, 36.

While the disclosure is given with reference to a particular type switch sanitizing device, it is to be understood that the disclosure relates to all types of switch sanitizing devices that locally sanitize contact surfaces in a localized or surrounded volume, using germicidal EM radiation, while allowing manual access to said contact surface so as to allow manual actuation of an electrical or electronic switch, while minimizing the escape of said germicidal EM radiation to levels that are not hazardous to humans or animals as the light source is configured to have an angle of incidence between 2° and 90° and exposes the contact surface(s) to be sanitized to more than 2,000 µW-s/cm² per treatment regime, while limiting exposure outside the region to be sanitized to less than 2,000 µW-s/cm² per interaction with said switch.

The invention claimed is:

1. A switch sanitizing device, comprising:
   a plate defining a switch aperture;
   a switch extending through the switch aperture, wherein the switch is moveable between an off-position and an on-position;
   a first sanitizing source positioned on the device such that UV electromagnetic radiation from the first sanitizing source is directed to a first contact surface area on the switch; and
   a second sanitizing source positioned on the device such that UV electromagnetic radiation from the second sanitizing source is directed to a second contact surface area on the switch.

2. The switch sanitizing device of claim 1, wherein the first sanitizing source comprises a first housing positioned in the plate and a first light source, and wherein the first light source generates UV electromagnetic radiation that is directed through a first aperture in the plate and into the first housing.

3. The switch sanitizing device of claim 2, wherein the UV electromagnetic radiation is redirected by a reflective surface within the first housing and toward the first contact surface area on the switch.

4. The switch sanitizing device of claim 3, wherein the first housing defines a conical shape defining an open end facing the switch.

5. The switch sanitizing device of claim 3, wherein the second sanitizing source comprises a second housing positioned in the plate and a second light source, and wherein the second light source generates UV electromagnetic radiation that is directed through a second aperture in the plate and into the second housing.

6. The switch sanitizing device of claim 5, wherein the UV electromagnetic radiation is redirected by a reflective surface within the second housing and toward the second contact surface area on the switch.

7. The switch sanitizing device of claim 6, wherein the second housing defines a conical shape defining an open end facing the switch.

8. The switch sanitizing device of claim 1, wherein the first contact surface area and the second contact surface area have an anti-reflective coating thereon.

9. The switch sanitizing device of claim 1, wherein the switch is connected to an electrical switch, wherein the electrical switch is electrically connected in a manner such that when the switch is in the on-position, the first sanitizing source is powered and the second sanitizing source is electrically isolated.

10. The switch sanitizing device of claim 9, wherein the first sanitizing source is positioned on the device such that the switch is oriented closer to the first sanitizing source than the second sanitizing source when in the on-position.

11. The switch sanitizing device of claim 10, wherein the first contact surface area on the switch is angled toward the plate when in the on-position having a primary angle of incidence between 2° and 90°.

12. The switch sanitizing device of claim 10, wherein the electrical switch is electrically connected in a manner such that when the switch is in the off-position, the second sanitizing source is powered and the first sanitizing source is electrically isolated.

13. The switch sanitizing device of claim 12, wherein the second sanitizing source is positioned on the device such that the switch is oriented closer to the second sanitizing source than the first sanitizing source when in the off-position.

14. The switch sanitizing device of claim 13, wherein the second contact surface area on the switch is angled toward the plate when in the off-position having a primary angle of incidence equal to or more than 2° and equal to or less than 90°.

15. The switch sanitizing device of claim 1, wherein at least 90% of the UV electromagnetic radiation is contained within the device.

16. The switch sanitizing device of claim 1, wherein at least 98% of the UV electromagnetic radiation is contained within the device.

17. The switch sanitizing device of claim 1, wherein the UV electromagnetic radiation is UV C electromagnetic radiation, having a significant portion of the electromagnetic radiation with a wavelength of 100 nm to 400 nm.

18. The switch sanitizing device of claim 1, wherein the UV electromagnetic radiation is UV C electromagnetic radiation, having a significant portion of the electromagnetic radiation with a wavelength of 200 to 300 nm.

19. The switch sanitizing device of claim 1, wherein the UV electromagnetic radiation is UV C electromagnetic radiation, having a significant portion of the electromagnetic radiation with a wavelength of 250 nm to 260 nm.

20. The switch sanitizing device of claim 1, wherein the total exposure of the contact surface to be sanitized receives more than 2,000 µW-s/cm² per treatment regime, while limiting exposure outside the region to be sanitized to less than 2,000 µW-s/cm² per interaction with said switch.

* * * * *